(12) United States Patent
Trieu

(10) Patent No.: US 6,733,531 B1
(45) Date of Patent: May 11, 2004

(54) ANCHORING DEVICES AND IMPLANTS FOR INTERVERTEBRAL DISC AUGMENTATION

(75) Inventor: Hai H. Trieu, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 196 days.

(21) Appl. No.: 09/693,880

(22) Filed: Oct. 20, 2000

(51) Int. Cl.⁷ .................................................. A61F 2/44
(52) U.S. Cl. ................... 623/17.11; 623/17.16; 606/61
(58) Field of Search ................. 623/17, 17.11, 623/17.12, 17.15, 17.16; 606/61

(56) References Cited

U.S. PATENT DOCUMENTS

| | | | |
|---|---|---|---|
| 3,867,728 A | 2/1975 | Stubstad et al. | 3/1 |
| 3,875,595 A | 4/1975 | Froning | 3/1 |
| 4,309,777 A | 1/1982 | Patil | 3/1 |
| 4,349,921 A | 9/1982 | Kuntz | 3/1 |

(List continued on next page.)

FOREIGN PATENT DOCUMENTS

| | | |
|---|---|---|
| EP | 0 700 671 A1 | 3/1996 |
| FR | 97 13056 / 2 769 827 | 10/1997 |
| WO | WO 90/11740 | 10/1990 |
| WO | WO 95/31946 | 11/1995 |
| WO | WO 96/01598 | 1/1996 |
| WO | WO 97/26847 | 7/1997 |
| WO | WO 97/37620 | 10/1997 |
| WO | WO 98/04217 | 2/1998 |
| WO | WO 02/17824 A2 | 3/2002 |

Primary Examiner—David H. Willse
Assistant Examiner—Kamrin Landrem
(74) Attorney, Agent, or Firm—Woodard, Emhardt, Moriarty, McNett & Henry LLP

(57) ABSTRACT

Devices for anchoring spinal implants in an intervertebral disc space are provided. Spinal implants are also provided that are resistant to lateral deformation. The implants may include a flexible peripheral supporting band disposed circumferentially about an elastic body. Methods for anchoring spinal implants and methods for reducing deformation of spinal implants are also provided.

11 Claims, 19 Drawing Sheets

U.S. PATENT DOCUMENTS

| | | | |
|---|---|---|---|
| 4,759,766 A | 7/1988 | Beuttner-Janz et al. | 623/17 |
| 4,759,769 A | 7/1988 | Hedman et al. | 623/17 |
| 4,772,287 A | 9/1988 | Ray et al. | 623/17 |
| 4,863,477 A | 9/1989 | Monson | 623/17 |
| 4,874,389 A | 10/1989 | Downey | 623/17 |
| 4,904,260 A | 2/1990 | Ray et al. | 623/17 |
| 4,911,718 A | 3/1990 | Lee et al. | 623/17 |
| 4,917,704 A | 4/1990 | Frey et al. | 623/17 |
| 4,932,969 A | 6/1990 | Frey et al. | 623/17 |
| 4,946,378 A | 8/1990 | Hirayama et al. | 623/17 |
| 4,955,908 A | 9/1990 | Frey et al. | 623/17 |
| 4,997,432 A | 3/1991 | Keller | 606/61 |
| 5,002,576 A | 3/1991 | Fuhrmann et al. | 623/17 |
| 5,035,716 A | 7/1991 | Downey | 623/17 |
| 5,047,055 A | 9/1991 | Bao et al. | 623/17 |
| 5,059,193 A * | 10/1991 | Kuslich | 606/61 |
| 5,071,437 A | 12/1991 | Steffee | 623/17 |
| 5,108,438 A | 4/1992 | Stone | 623/17 |
| 5,171,280 A | 12/1992 | Baumgartner | 623/17 |
| 5,192,326 A | 3/1993 | Bao et al. | 623/17 |
| 5,306,307 A | 4/1994 | Senter et al. | 623/17 |
| 5,306,308 A | 4/1994 | Gross et al. | 623/17 |
| 5,370,697 A | 12/1994 | Baumgartner | 623/17 |
| 5,401,269 A | 3/1995 | Buttner-Janz et al. | 623/17 |
| 5,423,816 A | 6/1995 | Lin | 606/61 |
| 5,425,773 A | 6/1995 | Boyd et al. | 623/17 |
| 5,458,642 A | 10/1995 | Beer et al. | 623/18 |
| 5,507,816 A | 4/1996 | Bullivant | 623/17 |
| 5,534,028 A | 7/1996 | Bao et al. | 623/17 |
| 5,534,030 A | 7/1996 | Navarro et al. | 623/17 |
| 5,545,229 A | 8/1996 | Parsons et al. | 623/17 |
| 5,549,679 A | 8/1996 | Kuslich | 623/17 |
| 5,556,431 A | 9/1996 | Buttner-Janz | 623/17 |
| 5,562,738 A | 10/1996 | Boyd et al. | 623/17 |
| 5,571,189 A | 11/1996 | Kuslich | 623/17 |
| 5,645,597 A | 7/1997 | Krapiva | 623/17 |
| 5,674,294 A | 10/1997 | Bainville et al. | 623/17 |
| 5,674,295 A | 10/1997 | Ray et al. | 623/17 |
| 5,674,296 A | 10/1997 | Bryan et al. | 623/17 |
| 5,683,464 A | 11/1997 | Wagner et al. | 623/17 |
| 5,683,465 A | 11/1997 | Shinn et al. | 623/17 |
| 5,693,100 A | 12/1997 | Pisharodi | 623/17 |
| 5,702,450 A | 12/1997 | Bisserie | 623/17 |
| 5,716,416 A | 2/1998 | Lin | 623/17 |
| 5,755,796 A | 5/1998 | Ibo et al. | 623/17 |
| 5,755,797 A | 5/1998 | Baumgartner | 623/17 |
| 5,824,093 A | 10/1998 | Ray et al. | 623/17 |
| 5,824,094 A | 10/1998 | Serhan et al. | 623/17 |
| 5,827,328 A | 10/1998 | Buttermann | 623/17 |
| 5,888,226 A | 3/1999 | Rogozinski | 623/17 |
| 5,893,889 A | 4/1999 | Harrington | 623/17 |
| 5,895,428 A | 4/1999 | Berry | 623/17 |
| 5,976,186 A | 11/1999 | Bao et al. | 623/17 |
| 6,001,130 A | 12/1999 | Bryan et al. | 623/17 |
| 6,093,205 A | 7/2000 | McLeod et al. | 623/17 |
| 6,120,503 A | 9/2000 | Michelson | 606/61 |

\* cited by examiner

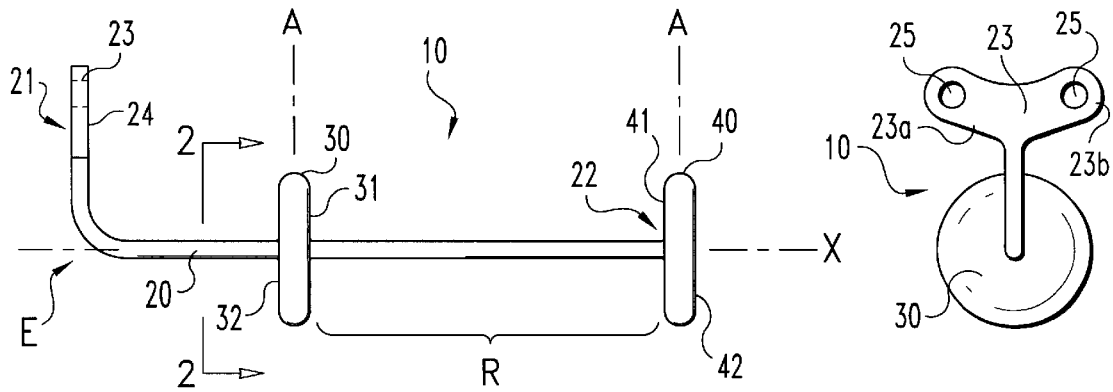
Fig. 1  Fig. 2
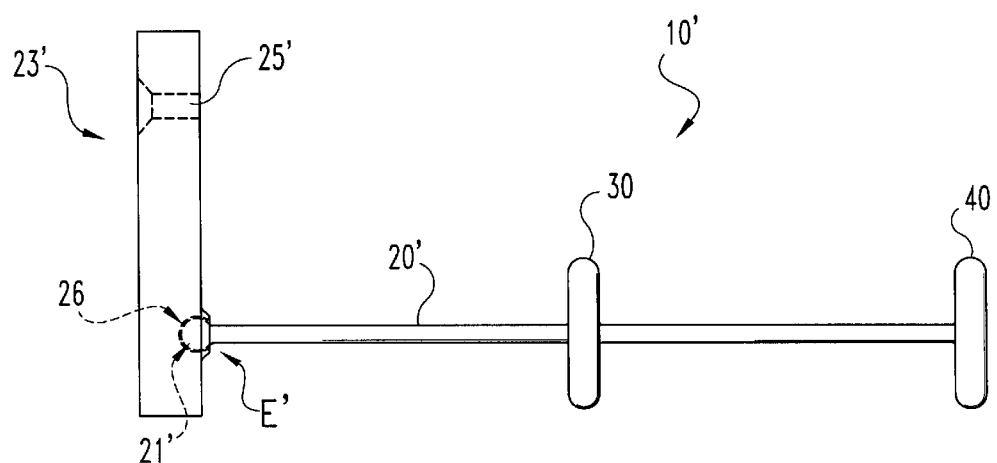
Fig. 3

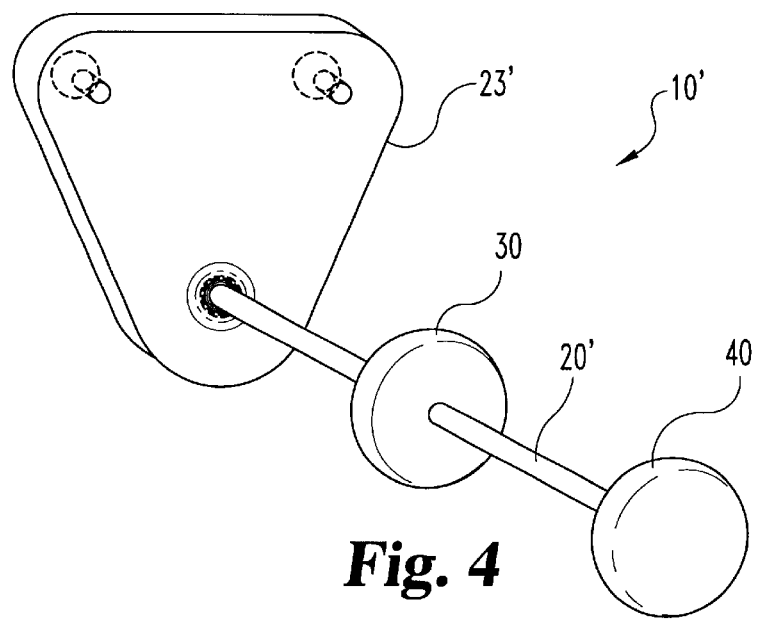
Fig. 4
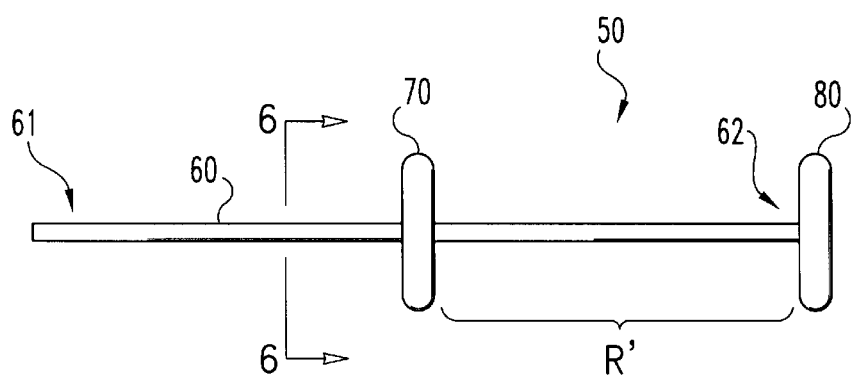 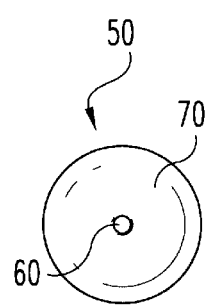
Fig. 5　　　　Fig. 6

ANCHORING DEVICES AND IMPLANTS FOR INTERVERTEBRAL DISC AUGMENTATION

BACKGROUND OF THE INVENTION

The present invention relates to spinal implants, devices for anchoring, and methods for implantation of, such implants in an intervertebral disc space.

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

Intervertebral discs may be displaced or damaged due to trauma or disease. Disruption of the annulus fibrosis allows the nucleus pulposus to protrude into the spinal canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process. As a disc dehydrates and hardens, the disc space height will be reduced, leading to instability of the spine, decreased mobility and pain.

One way to relieve the symptoms of these conditions is by surgical removal of a portion or all of the intervertebral disc. The removal of the damaged or unhealthy disc may allow the disc space to collapse, which could lead to instability of the spine, abnormal joint mechanics, nerve damage, as well as severe pain. Therefore, after removal of the disc, adjacent vertebrae are typically fused to preserve the disc space.

Several devices exist to fill an intervertebral space following removal of all or part of the intervertebral disc in order to prevent disc space collapse and to promote fusion of adjacent vertebrae surrounding the disc space. Even though a certain degree of success with these devices has been achieved, full motion is typically never regained after such intervertebral fusions. Attempts to overcome these problems has led to the development of disc replacements. Many of these devices are complicated, bulky and made of a combination of metallic and elastomeric components and thus never fully return the full range of motion desired. More recently, efforts have been directed to replacing the nucleus pulposus of the disc with a similar gelatinous material, such as a hydrogel. However, once positioned in the disc space, many hydrogel implants may migrate in the disc space and/or may be expelled from the disc space through an annular defect. Closure of the annular defect, or other opening, using surgical sutures or staples following implantation is typically difficult and, in some cases, ineffective. Moreover, such hydrogel implants may be subject to extensive deformation. Additionally, such hydrogel implants typically lack mechanical strength at high water content and are therefore more prone to excessive deformation, creep, cracking, tearing or other damage under fatigue loading conditions.

A need therefore exists for more durable nucleus pulposus or other spinal implants, including implants that are less resistant to deformation, as well as devices and methods that anchor the implants so that the implants are more resistant to migration and/or expulsion through an opening in the annulus fibrosis. The present invention addresses these needs.

SUMMARY OF THE INVENTION

Devices for anchoring a spinal implant in an intervertebral disc space are provided. In one form of the invention, a device includes an elongated anchoring body, such as an anchoring rod, and at least one securing member attached to the anchoring rod. The anchoring body or rod is configured to anchor, hold, or otherwise retain a spinal implant. In certain forms of the invention wherein more than one securing member is included, the securing members are spaced apart along the length of the anchoring rod and may define a region for disposing an implant therebetween. The anchoring rod has a first end and a second end, wherein the first end is securable to an adjacent vertebra. The anchoring devices may be made from metallic materials, non-metallic materials and combinations thereof.

Spinal implant systems are also provided that include the anchoring device described above and an elastic spinal implant. In certain forms of the invention, the anchoring devices include an anchoring rod and at least one securing member attached to the anchoring rod. The anchoring rod includes a first end, a second end, a longitudinal axis and extends at least partially through the implant. The anchoring component is securable to an adjacent vertebra. In one form of the invention, the securing members may be external to the implant, while in other forms of the invention the securing members may be internal to the implant or may be both internal and external to the implant.

Spinal implants are also provided that are resistant to lateral deformation as they are restrained, or otherwise reinforced, by a flexible, peripheral supporting band. In one form of the invention, the implant includes an elastic body sized for introduction into the intervertebral disc space. The elastic body includes an upper surface and a lower surface for contacting adjacent vertebral endplates. A flexible peripheral supporting band is disposed circumferentially about the elastic body to reduce deformation of the body. At least a portion of the upper and lower surfaces of the elastic body are free of the supporting band. The implant, including the band, is sized to fit within an intervertebral disc space which is at least partially defined by an annulus fibrosis.

Methods of anchoring a spinal implant are also provided. A preferred method includes providing an elastic spinal implant and an anchoring component that includes the anchoring devices described above, extending the anchoring rod of the device at least partially through the implant, and securing the anchoring component to an adjacent vertebra.

Methods of reducing deformation of a spinal implant are also provided. In one embodiment, a method includes disposing a flexible peripheral supporting band circumferentially about the implants described above.

One object of the present invention is to provide devices for anchoring spinal implants so they will be resistant to excessive migration in, and/or expulsion from, the intervertebral disc space.

Yet another object of the invention is to provide spinal implant systems including an elastic spinal implant and an anchoring component for anchoring the implant.

A further object of the invention is to provide spinal implants that are more resistant to lateral deformation.

These and other objects and advantages of the present invention will be apparent from the descriptions herein.

BRIEF DESCRIPTION OF THE FIGURES

FIG. 1 is a side view of a device for anchoring a spinal implant in an intervertebral disc space.

FIG. 2 is an end view of the device of FIG. 1, taken along line 2—2.

FIG. 3 is a side view of an alternative embodiment of a device for anchoring a spinal implant in an intervertebral disc space, having a ball-and-socket joint.

FIG. 4 is a perspective view of the device of FIG. 3.

FIG. 5 depicts a side view of an alternative embodiment of a device for anchoring a spinal implant in an intervertebral disc space.

FIGS. 6 is an end view of the device of FIG. 5, taken along line 6—6.

DESCRIPTION OF THE PREFERRED EMBODIMENTS

Figure 7A:
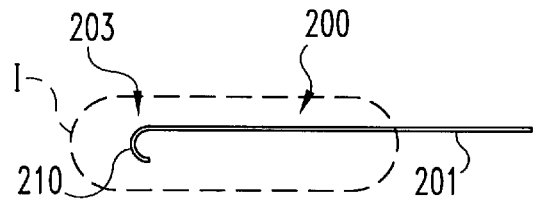
FIGS. 7A–7T depict top views of alternative embodiments of securing members of the anchoring devices described herein. The anchoring members are shown with a superimposed outline of how an implant I may be disposed on the anchoring device.
Figure 7B:
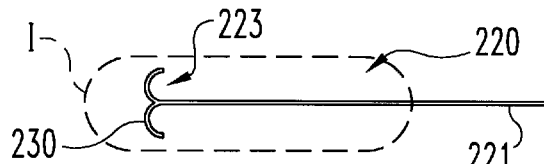
Figure 7C:
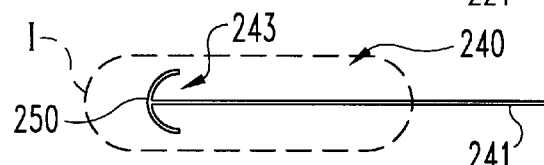
Figure 7D:
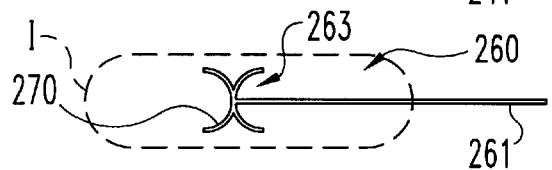

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention relates to devices for anchoring a spinal implant in an intervertebral disc space to prevent excessive migration in and/or expulsion from the disc space, as well as novel spinal implants. Spinal implant systems are also described that include the anchoring device as well as an anchored elastic spinal implant. The spinal implants described herein include those that may be useful as nucleus pulposus replacements, partial or complete disc replacements, and those that may be useful in other disc reconstruction or augmentation procedures.

In other aspects of the invention, spinal implants are provided that include an elastic body that is constrained and supported by a flexible supporting member, such-as a peripheral supporting band. The band may advantageously have high resistance to hoop stress, and may thus function in a similar manner as the annulus fibrosis. More particularly, the hoop stress in the band preferably increases exponentially after some small, allowable initial deformation. Such implants may advantageously be used where the integrity of the annulus fibrosis has been negatively affected, or in other circumstances wherein increased support of an implant is needed.

In one aspect of the invention, a device for anchoring a spinal implant in an intervertebral disc space is provided. The device may include an elongated anchoring body, such as an anchoring rod, having at least one securing member attached thereto, or otherwise disposed thereon. Referring now to FIGS. 1 and 2, anchoring device 10 may include an elongated anchoring body, or rod, 20, first securing member 30 and second securing member 40. Securing members 30 and 40 may oppose each other, may be spaced apart along the length of anchoring rod 20 and may define a region R for disposing a spinal implant therebetween. Moreover, the longitudinal axes A of the securing members preferably extend transverse with respect to the longitudinal axis X of the anchoring rod. The device may advantageously be secured to an adjacent vertebra.

For example, in one form of the invention, anchoring device 10 includes a first end 21 and a second end 22, wherein first end 21 is securable to an adjacent vertebra. First end 21 may define a bracket 23, or other similar structure, for securing first end 21 to an adjacent vertebra. Bracket 23 includes a vertebra-contacting surface 24 and at least one aperture 25 through which a bone screw, or other similar securing device, may be placed to secure the elongated body to an adjacent vertebra as more fully described below. Moreover, a screw securing mechanism, such as a lock screw or other known mechanism, may be used to further secure the screw so it will not back out, or otherwise loosen. Bracket 23 is shown as generally V-shaped in FIG. 2, although a wide variety of other shapes are contemplated, as long as first end 21 is securable in some form to an adjacent vertebra. As seen in FIG. 2, bracket 23 includes arm 23a and arm 23b. Arms 23a and 23b may be formed from one piece, or may be formed of more than one piece that are attached, or otherwise connected, to each other by methods known to the skilled artisan. Moreover, first end 21 may define a bracket that extends along the length of two adjacent vertebrae, so that the bracket may be secured both to an upper adjacent vertebra and to a lower adjacent vertebra in order to more stably secure anchoring rod 20, and ultimately to more stably secure a spinal implant.

In another form of the invention, the bracket described herein may be mounted on, or otherwise connected to, first end 21. For example, as shown in FIGS. 3 and 4, first end 21' of anchoring rod 20' may define a ball or other spherical-shaped end that fits in a socket 26 on bracket 23' to form a ball-and-socket joint, or ball joint. The ball joint advantageously allows further movement of the attached elongated body of anchoring device 10', which may reduce or eliminate stress that may otherwise exist near end E' of the elongated body.

Anchoring rod 20 may be formed from rigid, or otherwise non-flexible materials, including carbon fiber reinforced composite, such as carbon fiber/epoxy composites or carbon fiber/polyaryletherketone composites. Anchoring rod 20 may further be formed from a wide variety of metallic materials, including, for example, shape memory materials, stainless steel, titanium, titanium alloys, cobalt chrome alloys, and combinations thereof. The shape memory materials may be made from, for example, the nickel-titanium alloy known as Nitinol. The response of the shape memory material to deformation generally has two triggers as known in the art to induce the material to partially or fully recover its memorized shape. The first trigger is a thermal trigger where the deformed state is initially at a temperature such that the deformed state is stable. Upon heating, the temperature rises until the deformed state is no longer stable and begins to change to the memorized state. The second trigger is a stress-actuated trigger and may take advantage of superelasticity. The undeformed state is at a temperature such that at least some of the material is in the austenitic state. That is, the temperature may be such that the material is within the hysterisis loop responsible for the superelastic phenomenon or behavior. Under the influence of sufficient stress, the austenitic material will transform into the martensitic state. Upon the release of some or all of the stress, the temperature is such that the martensitic state is unstable and will automatically attempt to revert to the austenitic state with consequent shape reformation. It should also be understood that the shape memory material may attempt to recover the memorized shape by using some combination of thermal and stress actuation. Preferred shape memory materials will exhibit superelastic behavior. In devices formed from such rigid materials, anchoring rod 20 preferably includes an end E having an arcuate shape, as seen in FIG. 1, so that elongated body 20 may be secured to an adjacent vertebra.

The anchoring rod component of the device may also, in other forms of the invention, be formed of flexible materials so that the anchoring rod acts as a tether, or other flexible anchor. Such a flexible, anchoring rod component of an anchoring device 50 is shown in FIGS. 5 and 6. Flexible, anchoring rod 60 also includes a first securing member 70 and a second securing member 80. Anchoring rod 60 further includes a first end 61 and a second end 62, wherein the first end is securable to an adjacent vertebra. First end 61 may also define a bracket, such as bracket 23 as described above. First end 61 of anchoring rod 60 may also be mounted, or otherwise attached, to bracket 23' through a ball-and-socket joint as described above by modifying first end 61 appropriately. In preferred forms of the invention, first end 61 may be secured to an adjacent vertebra with an interference screw, especially when the device is implanted via a posterior approach as discussed below. Securing members 70 and 80 also define a region R' for disposing a spinal implant therebetween. Moreover, although rod 20 is shown as being cylindrical herein, it is realized that the rods described herein may assume a wide variety of shapes as known in the art, including pyramidal, square and other polygonal shapes. The shapes of the rods may be advantageously chosen so that the rods are effective in anchoring the implants described herein.

A wide variety of materials may be used to form flexible anchoring rod 60, including the same materials that may be used to form a rigid anchoring rod described above, although the thickness or diameter of the rod will be smaller than with the rigid rod so that the rod will be flexible. The metallic materials may be in the form of a wire, cable, chain or have some other appropriate configuration. Other suitable materials include non-metallic, polymeric materials, such as polyaryletherketone, polymethylmethacrylate, polycarbonate, polyurethane, silicone, polyolefins, including polytetrafluoroethylene, and combinations thereof; non-metallic, fiber or fabric materials, including cellulose, polyester, polyvinyl alcohol, polyacrylonitrile, polyamide, polytetrafluoroethylene, polyparaphenylene terephthalamide, polyolefins such as polyethylene, or from combinations of these materials. The polymeric materials may be braided, in the form of a cord, cable, or may have some other appropriate configuration, and combinations thereof. The elongated anchoring bodies described herein, as well as other portions of the anchoring component, may also be formed from a combination of flexible and rigid components. For example, bracket 23 or 23' of an elongated anchoring body may be formed from a non-flexible material whereas the remainder of the body may be formed from a flexible material. Other combinations are possible as one skilled in the art would be aware after reviewing the description herein.

The securing members may be either integral with the anchoring rod or may be otherwise attached thereto. Referring again to FIGS. 1 and 2, securing members 30 and 40 are disposed on anchoring rod 20 and include an inner surface 31 and 41, respectively, for contacting and securing a spinal implant, as well as an outer surface 32 and 42, respectively. As mentioned above, securing members 30 and 40 define a region R along anchoring rod 20 wherein a spinal implant may be disposed and secured. Thus, inner surfaces 31 and 41 of securing members 30 and 40, respectively, preferably abut the outer surface of an implant. The securing members may be attached to anchoring rod 20 in a variety of ways. For example, securing member 40 may include threads so that securing member 40 may be screwed onto an end 22 of anchoring rod 20 that is threaded. Moreover, the securing members may be attached with an adhesive, or other nonresorbable, biocompatible securing materials, including cyanoacrylate adhesive and epoxy glue. Furthermore, securing members may be secured by other means, including clamps, pins, knots, by friction fit, mechanical interlocking or combinations thereof.

Securing members 30, 40, 70 and 80 may, for example, be formed from the same materials as described above for the elongated anchoring body, or rod. In one preferred form of the invention, wherein the anchoring rod is formed from a flexible, non-rigid material, such as a braided fabric, the securing members may also be formed from fabric. For example, securing member 70 may be formed from a fabric that has been formed into a knot and secured to the anchoring rod and end 62 may be formed into, and otherwise define, a knot to form securing member 80.

As briefly mentioned above, the elongated body, or rod, of the anchoring device described herein may include at least one securing member, and may include two, three, four or more securing members disposed thereon or attached thereto. Furthermore, the securing members may be variously-shaped and may be configured to internally secure, externally secure, or both internally and externally secure an implant, including the implants described herein. Anchoring components that may be used to internally secure implants are shown, for example, in FIGS. 7A–7T.

Figure 7E:
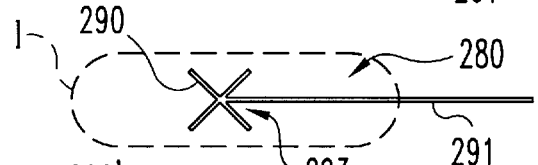
Figure 7F:
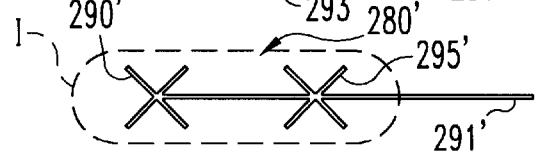
Figure 7G:
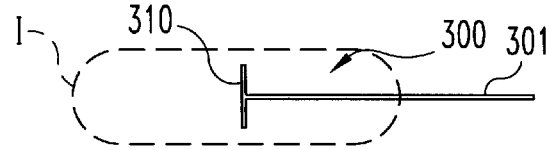
Figure 7H:
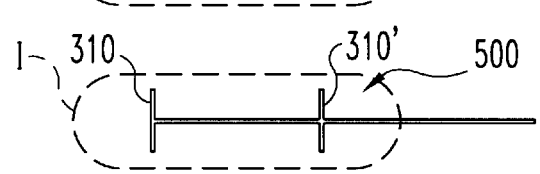
Figure 7I:
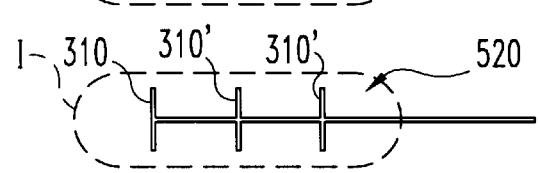

Referring now to FIGS. 7A–7D, anchoring devices (200, 220, 240, and 260) including elongated bodies, or anchoring rods (201, 221, 241, and 261, respectively) having a second end (203, 223, 243, and 263, respectively) defining at least one securing member (210, 230, 250 and 270, respectively), shaped in the form of one or more hooks are shown. FIG. 7E depicts an anchoring device 280 having a securing member 290 that includes at least one, preferably two or more, such as four, rod extending radially from second end 293 of anchoring rod 291. A multiplicity of such a set of four projecting rods, such as securing members 290' and 295', may be present, and may be spaced apart along the length of elongated member 291' of anchoring device 280' as seen in FIG. 7F. In alternative forms of the invention as seen in FIG. 7G, anchoring device 300 includes a single rod defining securing member 310 that has a longitudinal axis aligned transverse, in this case perpendicular, to the longitudinal axis of anchoring rod 301, although two or more of these extending rods 310 and 310', preferably separated along the length of elongated body 301 from each other, may be present as seen in FIGS. 7H and 7I (anchoring components 500 and 520, respectively). In these, as well as other forms of the invention, an adhesive or other similar agent that bonds, or otherwise secures the implant to the anchoring device may be disposed along the length of the elongated body that will be in contact with the implant to further secure the implant. The adhesive may further be used without any other securing member being present and may thus act as a securing member itself. Suitable adhesives include, for example, cyanoacrylate adhesives, epoxy adhesives and silicone adhesives.

Figure 7J:
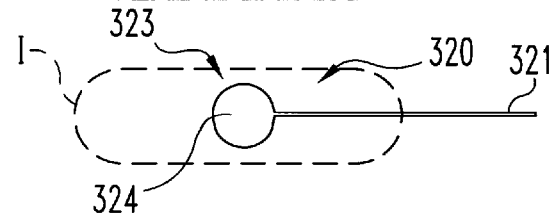
Figure 7K:
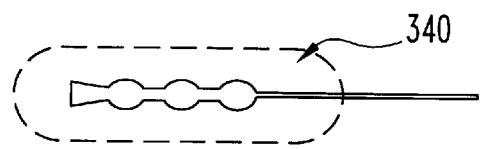
Figure 7L:
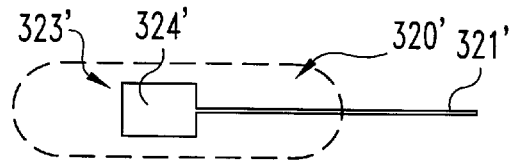
Figure 7M:
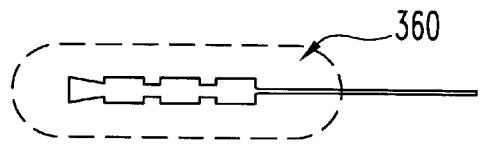
Figure 7N:
Figure 7O:
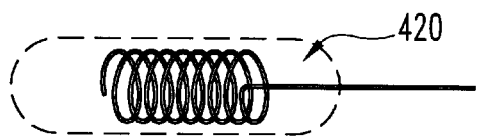
Figure 7P:
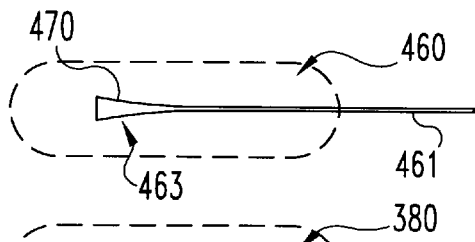
Figure 7Q:
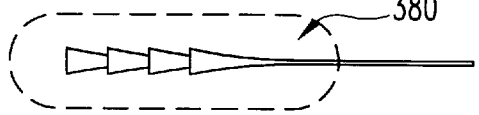
Figure 7R:
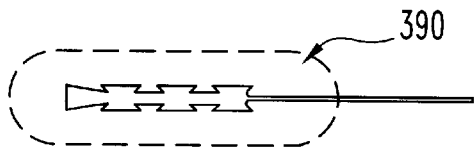
Figure 7S:
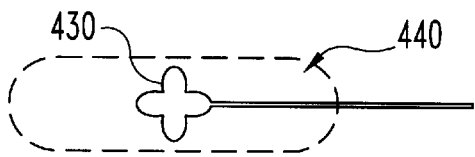

In other embodiments of the invention, second end 323 or 323' of elongated body 321 or 321' of anchoring component 320 or 320' may further define a spherical-shaped body 324 or a rectangular-shaped body 324' as seen in FIGS. 7J and 7L, respectively. A single spherical-shaped securing member may be present, or more than one member may be present wherein each securing member is preferably spaced apart along the length of the elongated body as seen, for example, in FIGS. 7K and 7M (anchoring devices 340 and 360). These configurations of the securing members may provide mechanical locking for increased fixation. Other anchoring components having securing members that may provide for mechanical locking include anchoring components 380 and 390 in FIGS. 7Q and 7R, respectively. In other forms of the invention, the second ends of the securing members of the anchoring components may further define sinusoidal or other wave shapes as seen in FIG. 7N (anchoring component 400) or may be a coiled, or spring element, (anchoring component 420) as seen in FIG. 7O. A multi-lobed securing member 430 is also encompassed as seen with anchoring component 440 in FIG. 7S. Moreover, securing member 470 may be defined by a tapered second end 463 of anchoring rod 461 of anchoring device 460 as seen in FIG. 7P.

Figure 7T:
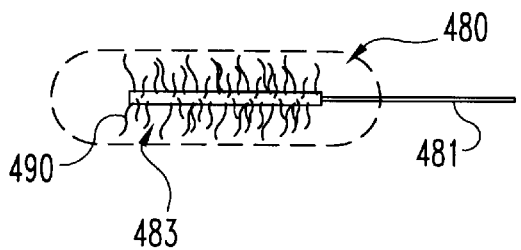

An anchoring device, such as anchoring device 480, may include securing members 490, such as fibers or other flexible elements, extending radially from anchoring rod 481, preferably from second end 483 of the anchoring rod as seen in FIG. 7T. It is realized that the anchoring devices described above having securing members that internally secure an implant may, if the implant is appropriately positioned on the anchoring device, act to externally secure, or both externally and internally secure, the implant.

Figure 8A:
FIGS. 8A–8H depict top views of further alternative embodiments of securing members of the anchoring devices described herein. The anchoring members are shown with a superimposed outline of how an implant I may be disposed on the anchoring device.
Figure 8B:
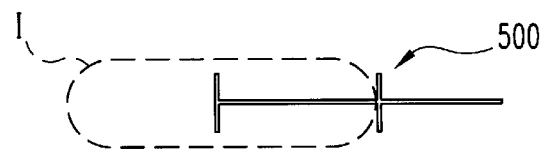

For example, anchoring device 300 may externally secure an implant as shown in FIG. 8A. Anchoring device 500 may be used to both internally and externally secure an implant as seen in FIG. 8B with appropriate adjustment in the spacing of the securing members and/or the size of the implant. Similarly, one skilled in the art would be aware that repositioning the implant on many of the anchoring devices described herein with internal securing members may provide for both internal and external securement of an implant.

Figure 8C:
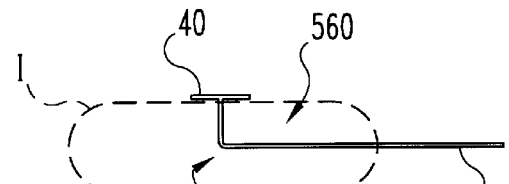
Figure 8D:
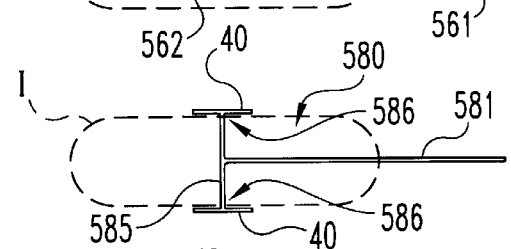
Figure 8E:
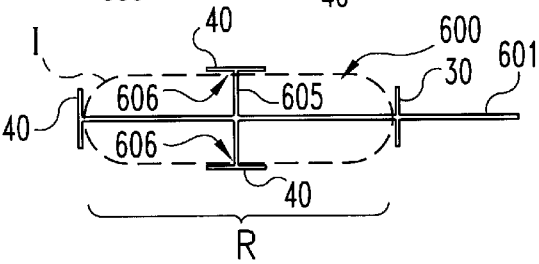
Figure 8F:
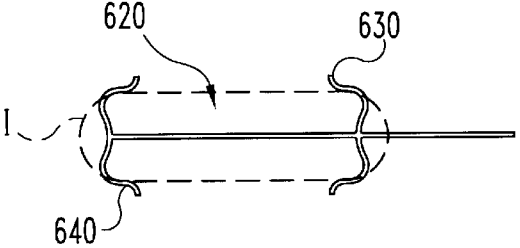
Figure 8G:
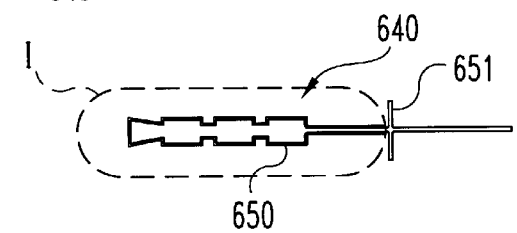

In yet other embodiments shown in FIGS. 8C–8E, anchoring devices with external securing members are shown, but may aid in internally securing an implant due to their construction. Anchoring device 560 includes an anchoring rod 561 that is bent at end 562 and is attached, or otherwise connected, to securing member 40, or other similar securing member as described herein. In a further form of the invention shown in FIG. 8D, anchoring device 580 includes an elongated anchoring body, or rod, 581 that connects, or otherwise attaches, to a connecting rod 585 preferably at a point equidistant from the ends 586 of the rod. Securing members, such as securing members 40, may be attached, or otherwise connected, to rod 585. Referring now to FIG. 8E, anchoring device 600 that includes an anchoring body 601 having opposing securing members, such as securing members 30 and 40, spaced along the length of the implant and defining a region R for disposing an implant therebetween is depicted. A connecting member, or bar 605 is attached to the anchoring rod in region R, preferably at a point equidistant from ends 606 of the bar and preferably extends radially from the anchoring body. Ends 606 of bar 605 are preferably connected to two other securing members, such as securing members 40. FIG. 8F depicts a variation of anchoring device 500 wherein securing members 630 and 640 of anchoring device 620 are wave-shaped and are therefore configured to extend through the implant they will secure. FIG. 8G depicts an anchoring device 640 that includes a combination of the mechanical locking features 650 similar to those previously described herein as well as an external securing element 651.

Figure 8H:
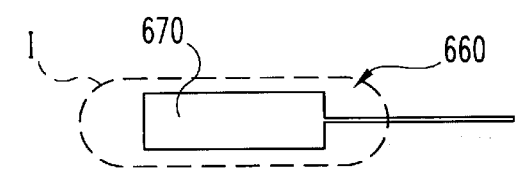

In other forms of the invention, an anchoring device is provided that helps to reinforce an implant to prevent the implant from undergoing excessive creep under high load. Referring now to FIG. 8H, anchoring device 660 includes internal securing member 670 that is rectangular-shaped and is sized to prevent the implant from undergoing excessive creep under high load. It is noted in all of FIGS. 7 and 8 that implant I is shown in outline to denote how the anchoring bodies may be positioned therein and it is realized that I may represent any of the implants described herein.

Figure 9:
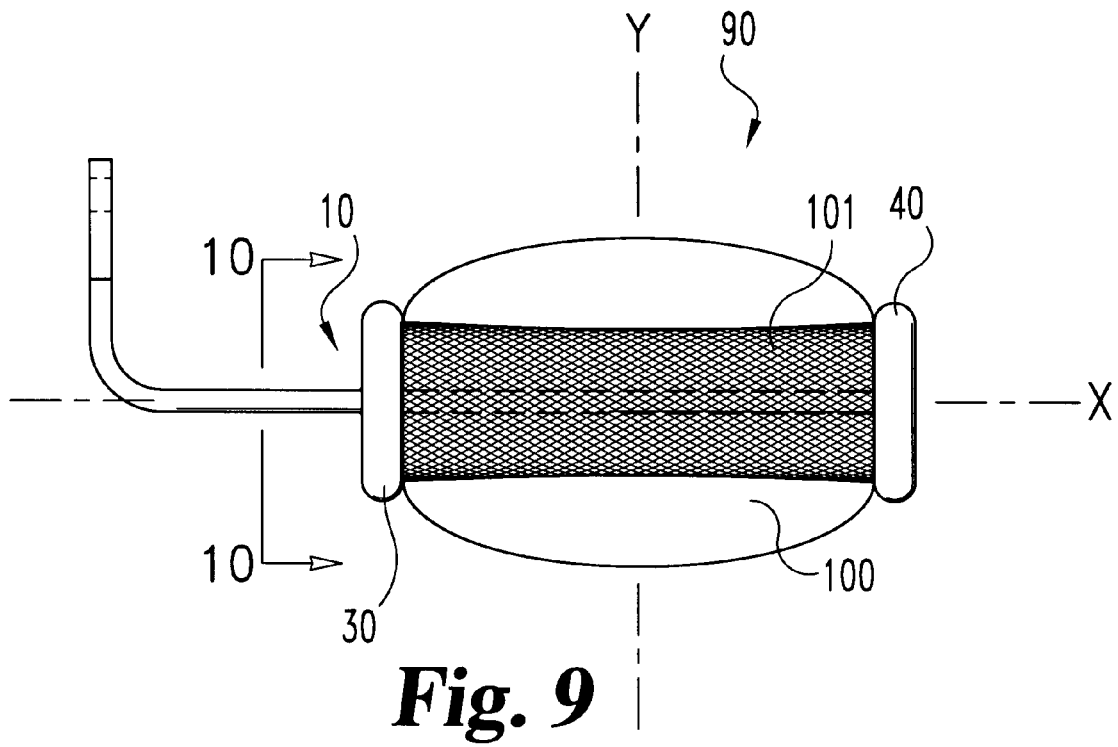
FIG. 9 is a side view of a spinal implant system.
Figure 10:
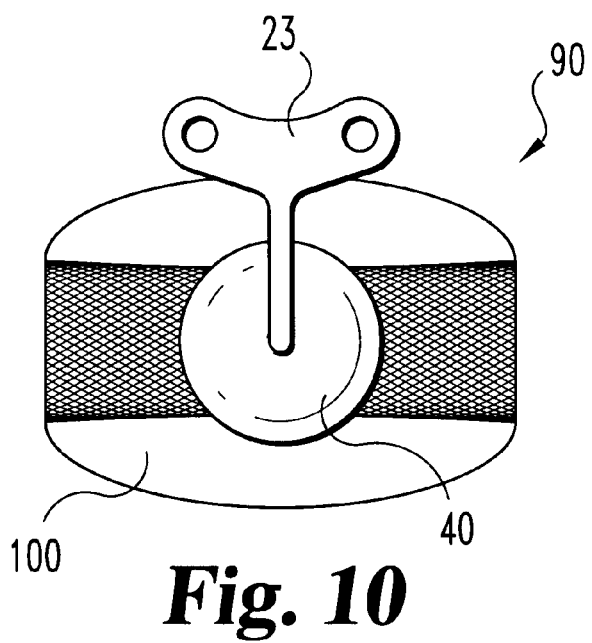
FIG. 10 depicts an end view of the system of FIG. 9, taken along line 10—10.
Figure 11:
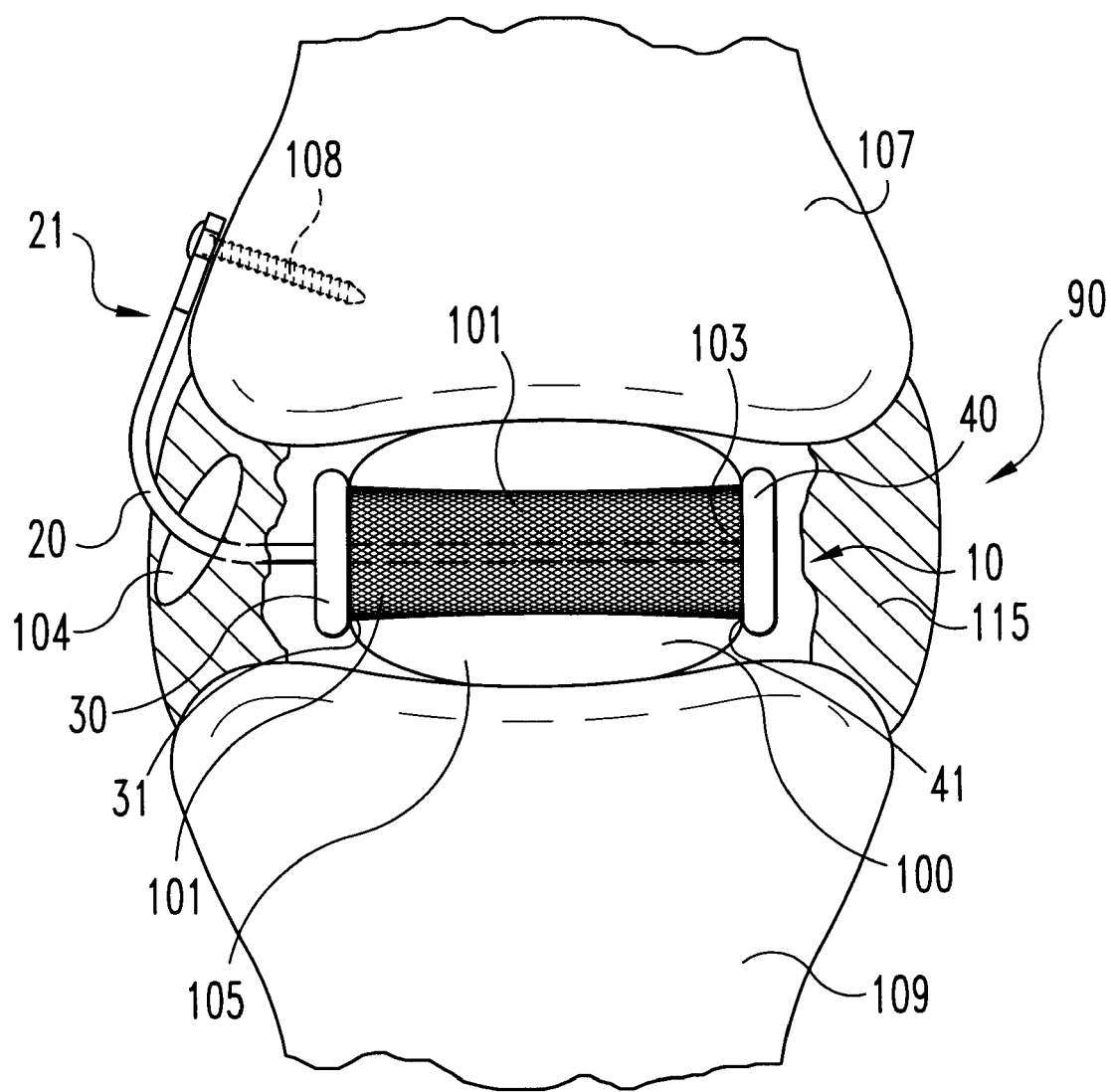
FIG. 11 depicts a side view of the spinal implant system of FIG. 9, implanted in an intervertebral disc space, that includes an anchoring component 10, an elastic body 100 and, optionally, a peripheral supporting band 101.

The devices described herein are advantageously utilized with a spinal implant, thus forming a spinal implant system. Referring now to FIGS. 9–11, spinal implant system 90 includes a spinal implant 100 and a spinal implant anchoring device 10 as described in reference to FIGS. 1 and 2. Inner surface 31 and 41 of securing members 30 and 40, respectively, abut outer surface 105 of implant 100. As seen in FIG. 11, anchoring rod 20 extends through aperture, or other defect, 104 in annulus fibrosis 115 so that the first end 21 of anchoring device 10 may be anchored to upper vertebra 107 with a bone screw 108. First end 21 may, of course, be anchored to lower vertebra 109, or may be secured to both vertebrae 107 and 109 if first end 21 is appropriately configured as discussed above. The longitudinal axis X of the rod may extend parallel to the longitudinal axis Y of the implant, but may extend through the implant in a wide variety of directions, as long as the rod functions to anchor the implant in the disc space. Furthermore, the anchoring rod preferably extends at least partially through the implant, but may extend completely through the implant, entering one location, such as an end, and exiting another location, such as another end, including an opposing end. In preferred forms of the invention, implant 100 may include a peripheral supporting band 101 as further described below to provide further lateral support for the implant, as well as to improve the strength of the implant. In one form of the invention, band 101 may have apertures, or other openings therethrough, on opposing sides of the band which are in contact with the securing member to allow the anchoring rod of the anchoring component, or device, to be placed therethrough. Moreover, implant 100 further includes a channel 103 extending therethrough through which the anchoring rod may be disposed. The implant is preferably molded such that the channel is formed during the molding process. However, the channel may be formed after formation of the implant in a variety of ways, including drilling to form a channel having a desired shape with an appropriate drill bit.

Figure 12:
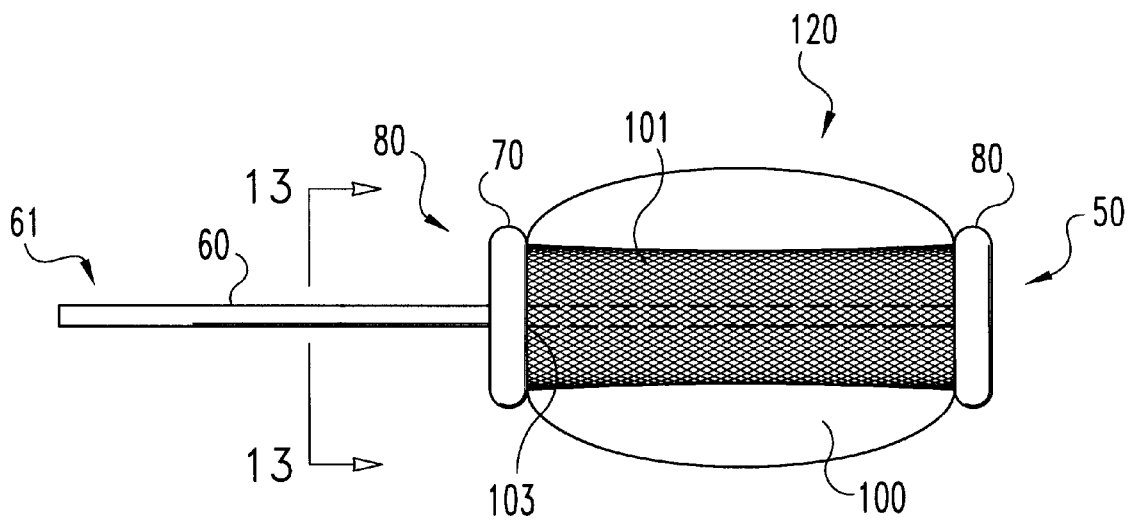
FIG. 12 depicts a side view of an alternative embodiment of a spinal implant system.
Figure 13:
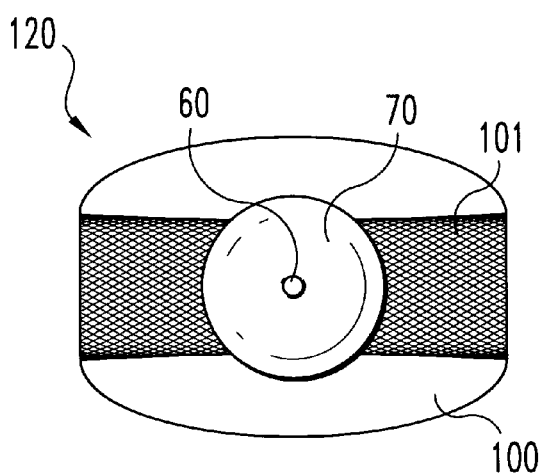
FIG. 13 depicts an end view of the system of FIG. 12, taken along line 13—13.
Figure 14:
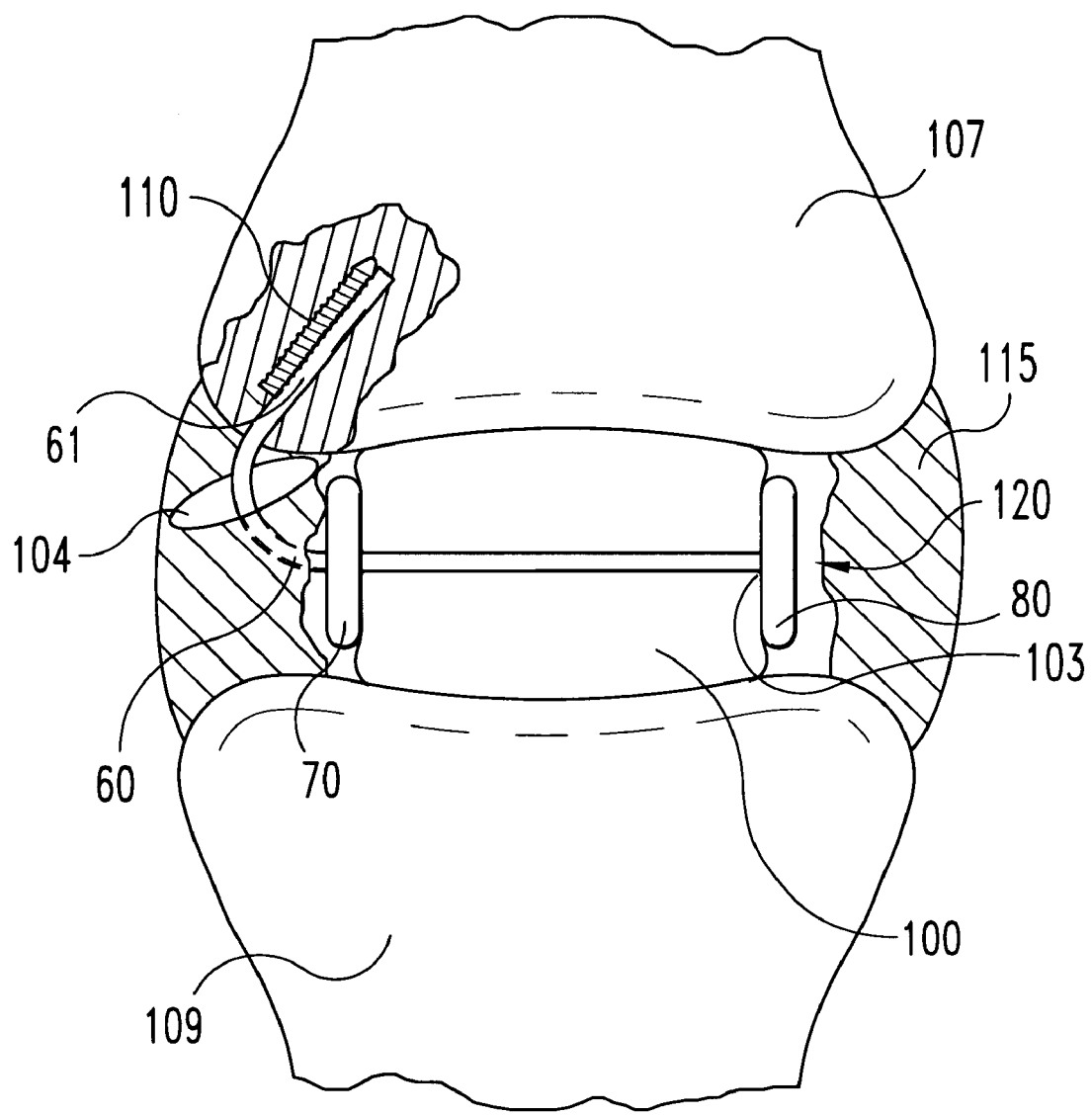
FIG. 14 depicts a side view of the system of FIG. 12 implanted in an intervertebral disc space.

Referring now to FIGS. 12–14 in another form of the invention, a spinal implant system 120 is shown which includes spinal implant 100 and spinal implant anchoring device 50. Anchoring rod 60 extends through aperture, or defect, 104 of annulus fibrosis 115. Furthermore, first end 61 of anchoring rod 60 of the anchoring device is secured to upper vertebra 107, but may be secured to lower vertebra 109, or both upper and lower vertebrae, with an interference screw 110 as more fully described below and as shown in FIG. 14. As seen in FIG. 14, one end of the anchoring rod is wedged between the screw and the bone. Furthermore, first end 61 of anchoring device 50 may be secured to both vertebra 107 and 109 for added stability if first end 61 is appropriately configured as discussed above.

The interference screws described herein can be non-resorbable, resorbable and made form a wide variety of materials, including metals, ceramics, polymers and combinations thereof. Non-resorbable metallic materials include stainless steels, cobalt chrome alloys, titanium, titanium alloys, shape memory materials as described above, especially those exhibiting superelastic behavior and including metals, and alloys thereof. Resorbable materials include polylactide, polyglycolide, tyrosine-derived polycarbonate, polyanhydride, polyorthoester, polyphosphazene, bioactive glass, calcium phosphate, such as hydroxyapatite, and combinations thereof. The anchoring devices may also be anchored with other soft tissue anchors known in the art, including suture anchors commonly used in arthroscopy or sports medicine surgeries, for example. In the case of a soft tissue or suture anchor, the end of the elongated body of the anchoring device is attached to the end of the anchor, which is embedded and anchored in an adjacent vertebral body.

A wide variety of spinal implants for serving differing functions may be anchored with the anchoring devices described herein, including implants sized and configured for nucleus pulposus replacements, sized and configured for partial or full disc replacements or other disc reconstruction or augmentation purposes. Elastic, or otherwise resilient, implants are most preferred. For example, implants may be formed from hydrophilic materials, such as hydrogels, or may be formed from biocompatible elastomeric materials known in the art, including silicone, polyurethane, polyolefins such as polyisobutylene and polyisoprene, copolymers of silicone and polyurethane, neoprene, nitrile, vulcanized rubber and combinations thereof. In a preferred embodiment, the vulcanized rubber is produced by a vulcanization process utilizing a copolymer produced, for example, as in U.S. Pat. No. 5,245,098 to Summers et al., from 1-hexene and 5-methyl-1,4-hexadiene. Preferred hydrophilic materials are hydrogels. Suitable hydrogels include natural hydrogels, and those formed from polyvinyl alcohol, acrylamides such as polyacrylic acid and poly (acrylonitrile-acrylic acid), polyurethanes, polyethylene glycol, poly(N-vinyl-2-pyrrolidone), acrylates such as poly (2-hydroxy ethyl methacrylate) and copolymers of acrylates with N-vinyl pyrolidone, N-vinyl lactams, acrylamide, polyurethanes and polyacrylonitrile or may be formed from other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyetherurethane, polycarbonate-urethane and silicone polyether-urethane. Other suitable hydrophilic polymers include naturally-occurring materials such as glucomannan gel, hyaluronic acid, polysaccharides, such as cross-linked carboxyl-containing polysaccharides, and combinations thereof. The nature of the materials employed to form the elastic body should be selected so the formed implants have sufficient load bearing capacity. In preferred embodiments, a compressive strength of at least about 0.1 MPa is desired, although compressive strengths in the range of about 1 MPa to about 20 MPa are more preferred.

Figure 15A:
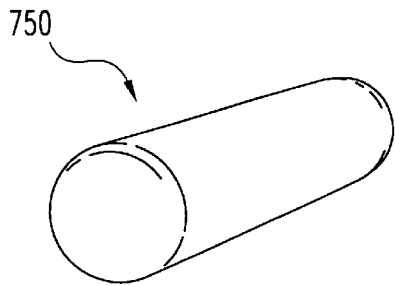
FIG. 15A depicts a perspective view of a spinal implant that may be anchored with the anchoring devices described herein.
Figure 15B:
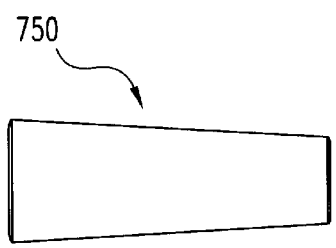
FIG. 15B depicts a side view of the implant of FIG. 15A.

The implants can be shaped as desired. For example, the nucleus pulposus implants may take the form of a cylinder, a rectangle, or other polygonal shape or may be substantially oval. The implants may include elastic bodies 750 that are tapered, such as at one end, as seen in FIGS. 15A and 15B, in order to create or maintain lordosis. Furthermore, in certain forms of the invention, the implants generally conform to the shape of the nuclear disc space. Additionally, implants can be sized to fit within an intervertebral disc space, preferably surrounded by an annulus fibrosis, or at least partially surrounded by an annulus fibrosis. That is, the implants preferably are of a height and have a diameter that approximates the height and diameter of an intervertebral disc space. In certain forms of the invention, a spinal implant may be a nucleus pulposus implant and may thus be sized to fit within the natural intervertebral disc space. In other embodiments, the spinal implants may be disc replacements as described herein, and may be sized to fit within the intervertebral disc space that includes the space resulting when the inner annulus fibrosis layer, or a portion thereof, is removed. Such a spinal implant would therefore be sized to fit within the larger intervertebral disc space that includes the space resulting from removal of a portion of the annulus fibrosis, and would thus typically have a width or diameter that is substantially larger than the natural nucleus pulposus.

Figure 16:
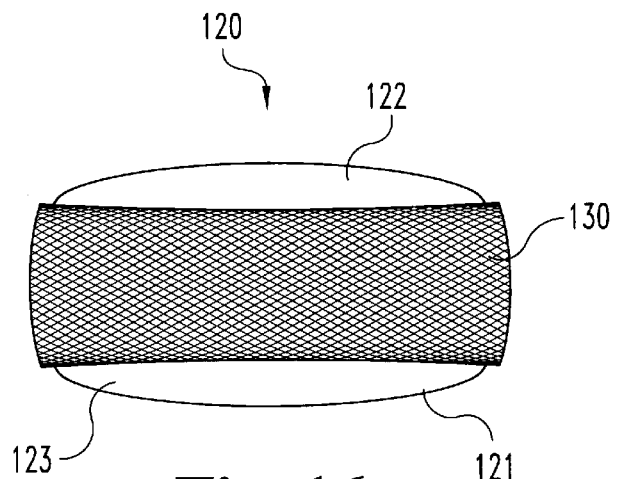
FIG. 16 is a side view of a spinal implant reinforced with a flexible peripheral supporting band.
Figure 17:
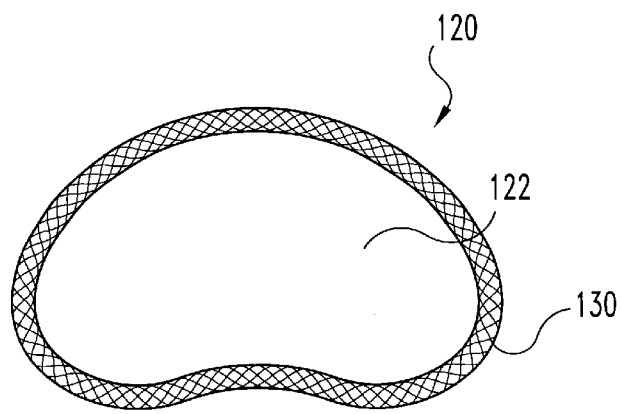
FIG. 17 depicts a top view of the implant of FIG. 16.

As mentioned above, the implant to be anchored preferably is reinforced for increased strength and to decrease lateral deformation of the implant. Accordingly, in yet another aspect of the invention, a reinforced spinal implant is provided. Referring now to FIGS. 16 and 17, implant 120 includes a load bearing elastic body 121 with an upper surface 122 and a lower surface 123. Implant 120 includes a preferably flexible, supporting member, such as peripheral supporting band 130 disposed circumferentially about body 121. Band 130 is similar to band 100 discussed above, with the exception that band 130 does not have openings therethrough on opposing sides of the band. As the implant, including the elastic body and supporting band, advantageously may replace all or a portion of the natural nucleus pulposus, while retaining the annulus fibrosis or a portion thereof, the implant may be sized to fit within the intervertebral disc space defined by the annulus fibrosis or a portion thereof.

As seen in FIG. 16, elastic body 121 includes upper and lower surfaces 122 and 123, respectively, portions of which are exposed to directly contact adjacent vertebral endplates. This exposure allows the lubricated upper and lower surfaces of elastic body 121 to articulate against the endplates to minimize abrasive wear of supporting band 130 and the endplates. Although the amount of the upper and lower surfaces of elastic body 121 that are exposed may vary, typically at least about 50%, preferably at least about 70%, more preferably at least about 80% and most preferably at least about 90% of the surfaces are exposed. In certain forms of the invention, the elastic body core may function as a nucleus pulposus, and thus functions as a load bearing component with stress transfer capabilities.

Figure 18A:
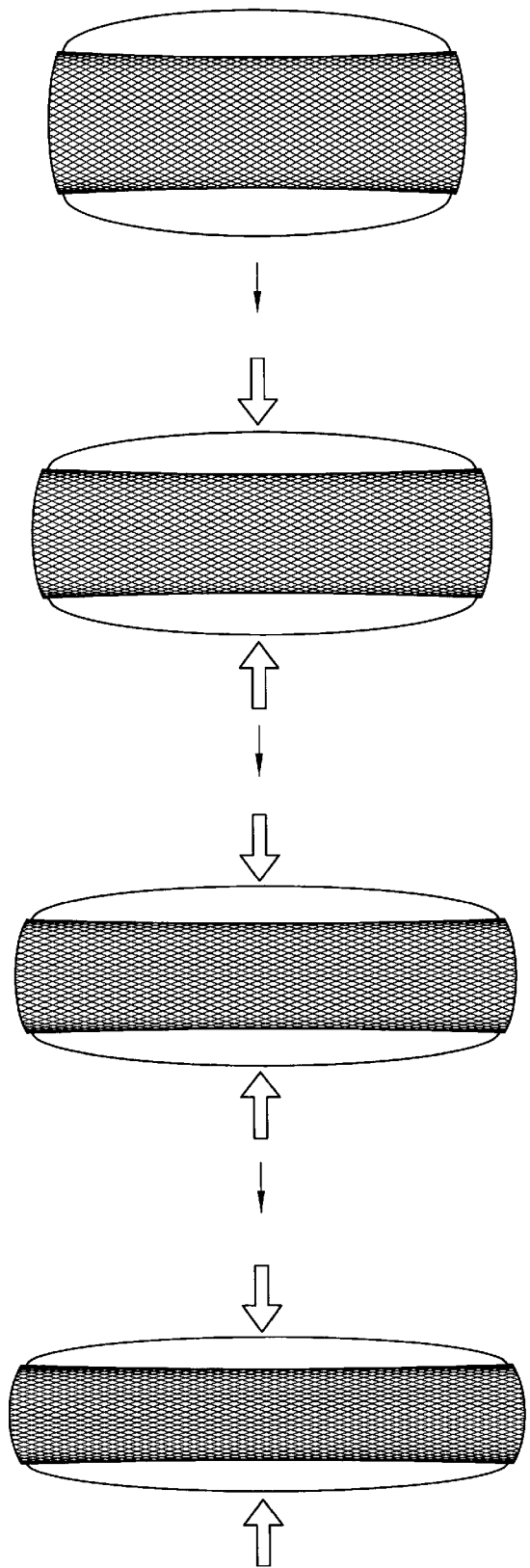
FIG. 18A shows the effect of imposing a load, represented by the darkened arrows, on the deformation of a spinal implant reinforced with a flexible supporting band. Top to bottom: no load; low load, moderate load; high load.
Figure 18B:
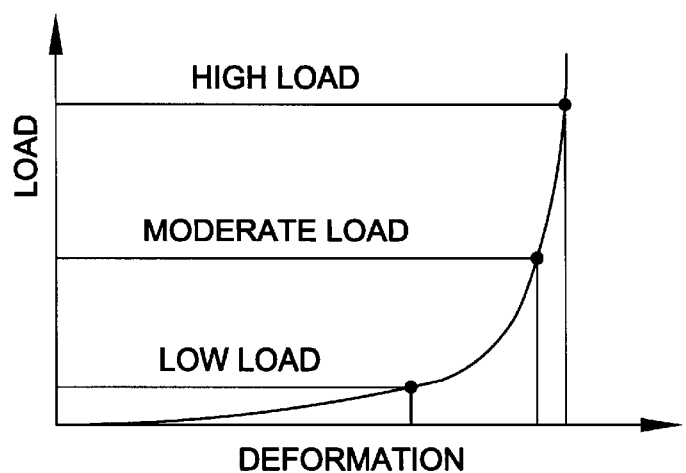
FIG. 18B is a graphical representation of the effect of imposing a load on the deformation of a spinal implant of FIG. 18A.
Figure 19A:
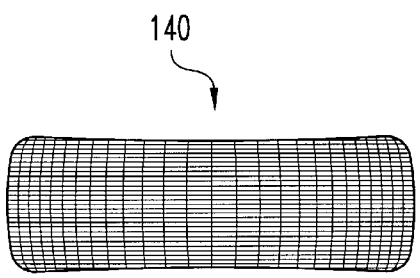
FIGS. 19A–19D depict alternative embodiments of a flexible peripheral supporting band of the present invention.
Figure 19B:
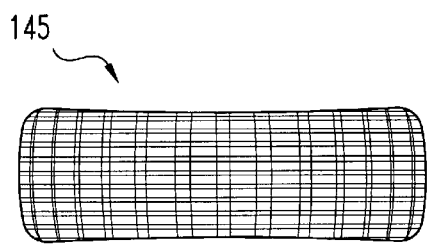
Figure 19C:
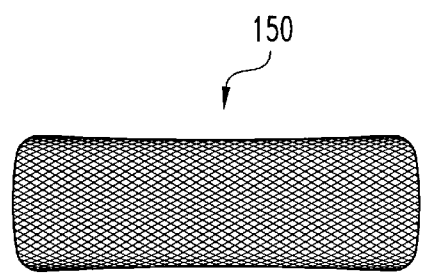
Figure 19D:
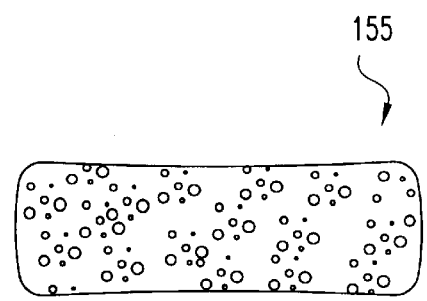

Peripheral supporting band 130 helps restrict excessive horizontal deformation of elastic body 121 upon loading conditions, as seen progressively in FIG. 18A, thereby helping to restore and maintain disc height. The hoop stress in the band increases exponentially after some small, initial deformation as seen in FIG. 18B. Band 130 preferably decreases lateral deformation, compared to deformation of an implant without the circumferential reinforcing band, as desired. Band 130 may, for example, decrease lateral deformation by at least about 20%, preferably at least about 40%, further preferably at least about 60%, more preferably at least about 80% and most preferably at least about 90%. An implant, such as one that includes an elastic body, having such a flexible supporting band, will be flexible and otherwise resilient to allow the natural movements of the disc and provides shock absorption capability at low to moderate applied stress, but will resist excessive deformation for disc height maintenance under high loading conditions. As described herein in the case of a lumbar disc, for example, low applied stress includes a force of about 100 Newtons to about 250 Newtons, moderate stress includes a force of about 250 Newtons to about 700 Newtons, and high loading conditions, or high stress, includes a force of about above 700 Newtons. Such a reinforced implant may be advantageously anchored with the anchoring devices described herein. Moreover, other outer covers, or jackets, as described in U.S. Pat. No. 5,674,295 may be utilized to reinforce implants to be anchored with the devices described herein. In preferred forms of the invention, the bands, jackets, or other outer covers or similar supporting members are flexible in that they may be folded or otherwise deformed, but are substantially inelastic so that the implant is more fully reinforced or otherwise supported.

Peripheral supporting band 130, as well as other outer covers, or jackets, may be made from a wide variety of biocompatible polymers, metallic materials, or combination of materials that form a strong but flexible support to prevent excessive lateral (horizontal) deformation of the core under increasing compressive loading. Suitable materials include non-woven, woven, braided, or fabric materials made from polymeric fibers including cellulose, polyethylene, polyester, polyvinyl alcohol, polyacrylonitrile, polyamide, polytetrafluoroethylene, polyparaphenylene terephthalamide, and combinations thereof. Other suitable materials include non-reinforced or fiber-reinforced elastomers such as silicone, polyolefins such as polyisobutylene and polyisoprene, polyurethane, copolymers of silicone and polyurethane, neoprene, nitrile, vulcanized rubber and combinations thereof. In a preferred form of the invention, a combination, or blend, of silicone and polyurethane is used. Furthermore, the vulcanized rubber is preferably produced as described above for the spinal implants. Supporting band 130 is advantageously made from materials described herein that allow it to be porous, which, in the case of an elastic body made from a hydrogel, or other hydrophilic material, allows fluid circulation through the elastic core body to enhance pumping actions of the intervertebral disc. Supporting members may further be formed from carbon fiber ceramic, ceramic fibers, metallic fibers, or other similar fibers described, for example, in U.S. Pat. No. 5,674,295, or from metallic materials that include shape memory materials as described above, especially those exhibiting superelastic behavior, titanium, titanium alloys, stainless steel, cobalt chrome alloys and combinations thereof. FIGS. 19A–19D show supporting bands of various patterns, including braided patterns (bands 140, 145 and 150) or porous patterns (band 155). It is realized that the braided materials may also be porous.

In addition to reinforcing the implants described herein with an outer cover, jacket or supporting band as described above, spinal implants 100, such as those formed from a hydrogel material, that are advantageously anchored with the anchoring devices described herein may be reinforced by forming the implant by molding hydrogels of different stiffness together and by annealing methods that include dipping the hydrogel in a hot oil bath, as described in U.S. Pat. No. 5,534,028. Other suitable reinforced spinal implants, such as nucleus pulposus implants, that may advantageously be used in the system of the present invention include those described in U.S. Pat. Nos. 5,336,551, as well as the novel implants described herein. As discussed above, the implant may be advantageously shaped to conform to the intervertebral disc space, or shaped as otherwise desired, as long as the implant has load bearing capability. Although the amount of load the implant is required to bear may vary depending on several factors, including the particular location in which the implant will be positioned, as well as the general health of the surrounding intervertebral discs, it is preferred that the implant be able to bear a load of at least about 20 Newtons for cervical discs, at least about 50 Newtons for thoracic discs and at least about 100 Newtons for lumbar discs.

Figure 20:
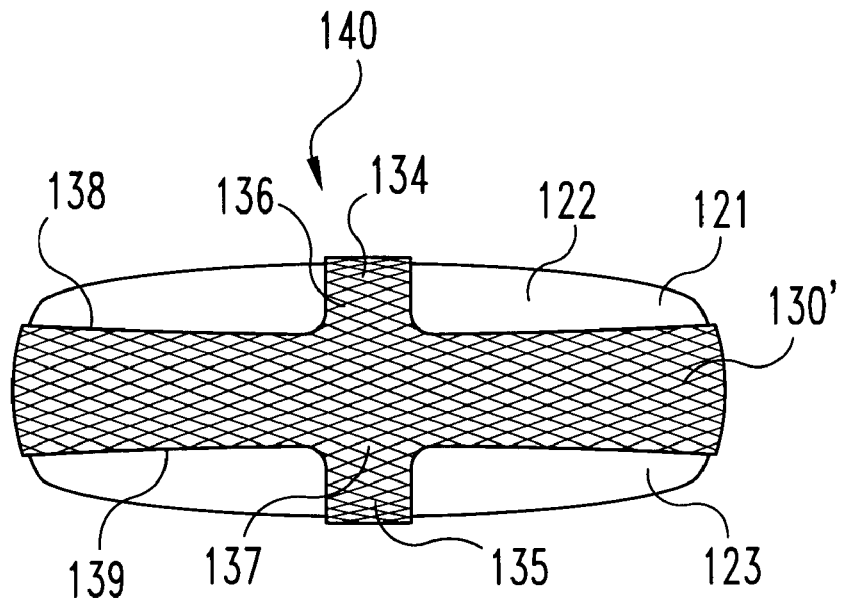
FIG. 20 depicts a side view of a spinal implant of the present invention that is reinforced, and otherwise supported, by peripheral supporting band 130' and straps 134 and 135.
Figure 21:
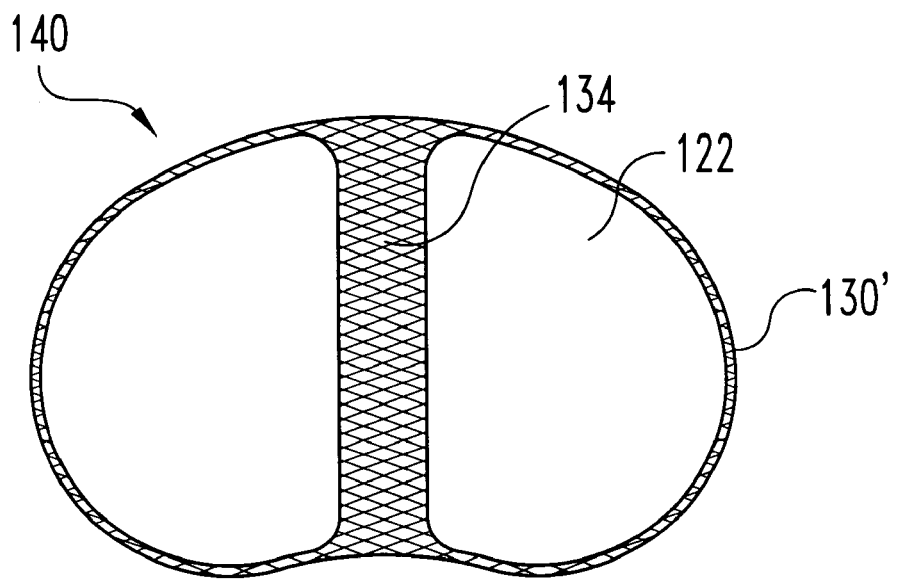
FIG. 21 shows a top view of the implant of FIG. 20.
Figure 22:
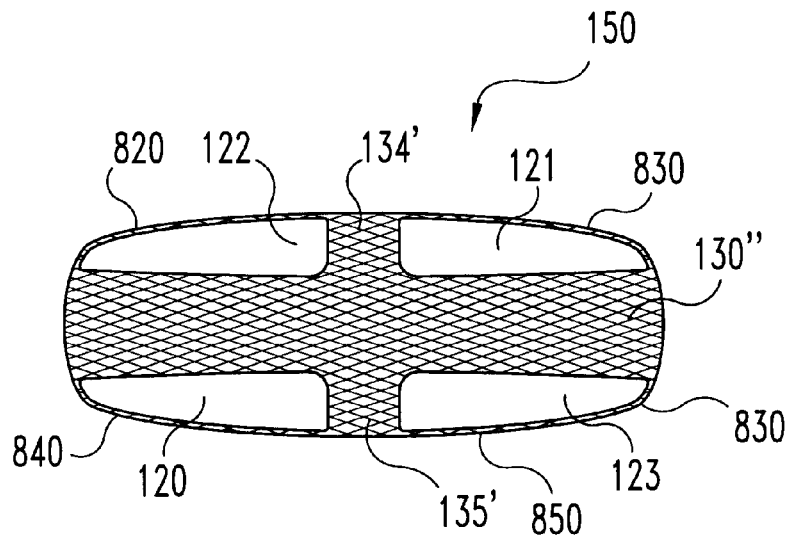
FIG. 22 depicts a side view of an alternative embodiment of a spinal implant of the present invention, that includes a peripheral supporting band 130" and securing straps 134', 135', 820, 830, 840 and 850.
Figure 23:
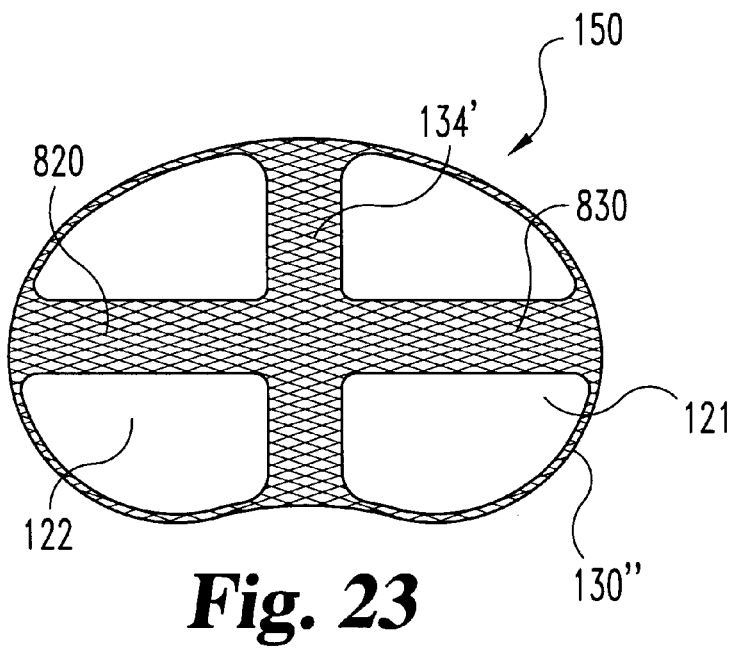
FIG. 23 depicts a top view of the implant of FIG. 22.

In yet other forms of the invention, an implant reinforced with a peripheral supporting band as described above is provided that is further reinforced with one or more straps. The straps may be advantageous in preventing the peripheral supporting band described herein from slipping, or otherwise sliding off the implant. Referring now to FIGS. 20 and 21, at least one strap 134 extends along upper surface 122 and at least one strap 135 extends along lower surface 123 of elastic body 121 of implant 140. Ends 136 of strap 134 and ends 137 of strap 135 are each preferably connected, or otherwise attached, to peripheral supporting band 130'. The point of attachment may be any location that will secure the strap, including at the upper margins 138 of the band, lower margins 139 of the band or any region between the upper and lower margins. Although two straps 134 and 135 are shown extending along upper surface 122 and lower surface 123, respectively, in FIGS. 20 and 21, one continuous strap may be utilized that extends completely around the implant, or the strap utilized may be in multiple pieces, as long as the combination of straps are sufficient to prevent excessive slipping and or sliding of the supporting band. Furthermore, more than one strap may extend along upper surface 122 and more than one strap may extend along lower surface 123. For example, as seen in FIGS. 22 and 23, straps 820, 830, 840 and 850 of implant 150 are attached to strap 130". Straps 820 and 830 are also attached to strap 134' and straps 840 and 850 are also attached to strap 135'.

As mentioned above, the spinal implant with the flexible peripheral supporting band may be anchored utilizing the anchoring devices described herein. In other forms of the invention, implants as described herein may be anchored with an outer, preferably resorbable, shell as described in U.S. patent application Ser. No. 09/650,525 to Trieu, filed Aug. 30, 2000. In further forms of the invention, the implant may further include various outer surface features that may further restrain movement of the implant in the intervertebral disc space, with or without the outer shell. Such surface features are also more fully described in U.S. patent application Ser. No. 09/650,525 to Trieu, filed Aug. 30, 2000.

Figure 24:
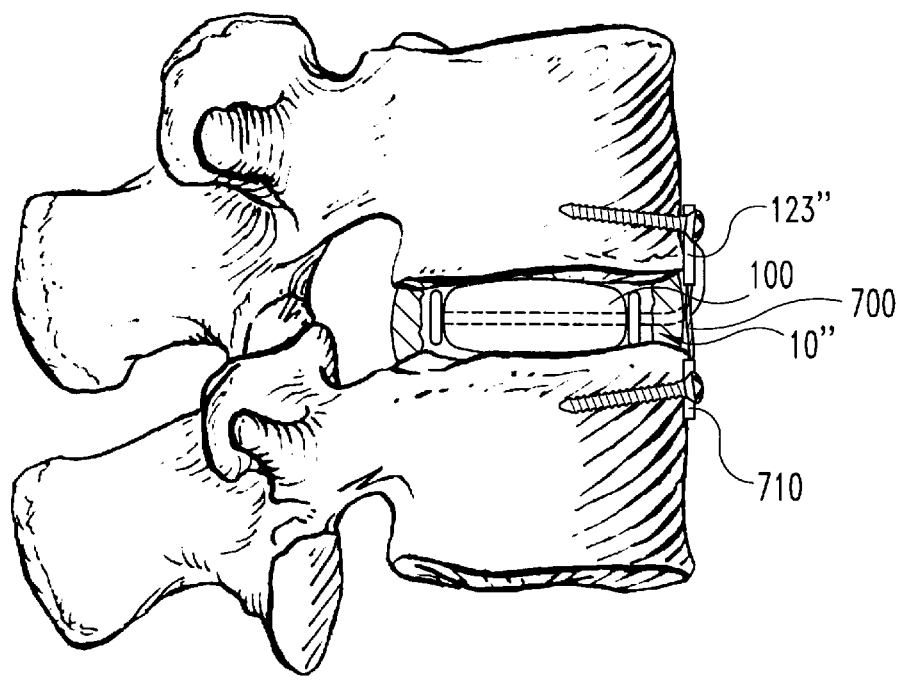
FIG. 24 shows a cut-away view of an alternative embodiment of an anchoring device implanted in an intervertebral disc space for anchoring implant 100 with a tension band 700 extending between vertebrae 107 and 109.
Figure 25:
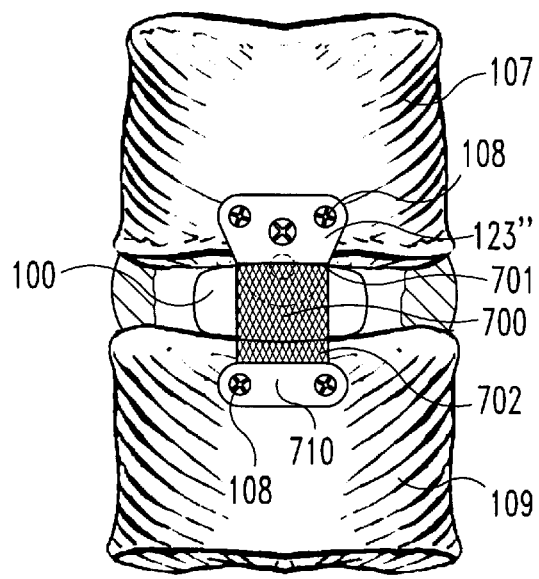
FIG. 25 depicts a side view of the device of FIG. 24.

In yet other forms of the invention, a tension band 700 may be secured to the anchoring device and to an adjacent vertebra to, for example, provide further stabilization of the device, especially wherein the annulus and/or the ligament surrounding the annulus at the defect site are compromised. Referring now to FIGS. 24 and 25, one end 701 of band 700 may be attached to an anchoring device, such as anchoring device 10" (similar to anchoring device 10 except that bracket 123" is utilized), at, for example, bracket 123", and the other end 702 may be secured to a plate 710, such as a metal plate, that is secured to the adjacent vertebra utilizing screws 108 as described herein. Band 700 may be attached to the anchoring device in a variety of ways, including crimping, tying, mechanical locking or may be secured with the same screws used to secure the anchoring device to the vertebral bodies. If two anchoring devices are utilized as described below, or if a single anchoring device is used that is secured to both adjacent vertebrae, one end 701 of tension band 700 may be attached to one of the brackets, or other areas, of the first anchoring device and the other end 702 of band 700 may be attached to the other bracket, or other area, of the second anchoring device. The tension band is preferably flexible to allow some degree of motion, but is substantially inelastic to prevent excessive extension.

The tension band may be formed from a wide variety of natural or synthetic tissue biocompatible materials. Natural materials include autograft, allograft and xenograft tissues. Synthetic materials include metallic materials and polymers. The metallic materials can be formed from shape memory alloy, including shape memory materials made from, for example, the nickel-titanium alloy known as Nitinol as described above. The shape memory materials may exhibit shape memory as described above, but preferably exhibit superelastic behavior. Other metallic materials include titanium alloy, titanium, stainless steel, and cobalt chrome alloy. Suitable polymeric materials include, for example, polyethylene, polyester, polyvinyl alcohol, polyacrylonitrile, polyamide, polytetrafluoroethylene, polyparaphenylene, terephthalamide and combinations thereof. The materials used to form the tension band can be in a variety of forms, including the form of a fiber, woven, or non-woven fabric, braided, bulk solid and combinations thereof. The tension band may further be treated, such as by coating and/or impregnating, with bioactive materials that may enhance tissue ingrowth and/or attachment, including hydroxyapatite, bioglass, and growth factors. Suitable growth factors include transforming growth factors, insulin-like growth factors, platelet-derived growth factors, fibroblast growth factors, bone morphogenetic proteins as further described herein and combinations thereof.

In yet another aspect of the invention, methods of anchoring a spinal implant are provided. In one form of the invention, a method includes providing an elastic spinal implant and an anchoring component as described herein. The elongated body, or anchoring rod, component of the anchoring component is at least partially extended, or otherwise disposed, through the implant. The implant may include a pre-formed channel therethrough, preferably formed during formation of the implant, through which the anchoring rod may be extended. In alternative embodiments, the implant may be formed around internal securing members as discussed above. The longitudinal axis of the anchoring rod may also extend parallel to the longitudinal axis of the implant, or any other direction as mentioned above that will allow the anchoring rod to anchor, secure, restrain or otherwise hold the implant in the disc space. As an example, the anchoring rod, as well as the securing members, may take a tortuous path through the implant, especially when the anchoring bodies have ends defining variously-shaped securing members, as more fully described above, with reference to, for example, FIGS. 7N, & 7O and 7T.

As further discussed above, in those forms of the invention wherein a securing member is at an end of the implant, the securing member may be attached after the elongated body component is extended through the implant. For example, with reference to FIGS. 1 and 7, securing member 40 may be attached to end 22 of elongated body 20 after anchoring rod 20 is extended through channel 103 of implant 100. Moreover, the securing member may also be formed after rod 20 is extended through channel 103, as in the case where securing member 40 is defined by a knot structure. In other forms of the invention, the channel may be formed after the implant is formed by forming a channel with an appropriate tool, such as a drill with an appropriately sized and shaped drill bit. One of the ends of the anchoring component are then secured to an adjacent vertebra.

In further aspects of the invention, methods of reducing deformation of a spinal implant are provided. In one embodiment, a method includes disposing a flexible peripheral supporting band as described above circumferentially about the implant.

The implants formed from a hydrogel, or other similar hydrophilic material described herein, including the supporting band of the reinforced implants, may advantageously deliver desired pharmacological agents. The pharmacological agent may include a growth factor that may advantageously repair a damaged annulus fibrosis, endplates or may have some other beneficial effect. A wide variety of growth factors may advantageously be employed in the present invention. For example, the growth factor may include a bone morphogenetic protein, transforming growth factors, such as transforming growth factor-β (TGF-β), insulin-like growth factors, platelet-derived growth factors, fibroblast growth factors, or other similar growth factor having the ability to repair the endplates, annulus fibrosis and/or nucleus pulposus of an intervertebral disc, or the ability to have some other beneficial effect. The growth factors, or other pharmacological agents, are typically included in the implant in therapeutically effective amounts. For example, the growth factors may be included in the implants in amounts effective in repairing an intervertebral disc, including repairing the endplates, annulus fibrosis and nucleus pulposus. Although these amounts will depend on the specific case, the implants may typically include no more than about five weight percent of the growth factors, and preferably no more than about one weight percent of the growth factors. In a preferred form of the invention, the growth factor is a bone morphogenetic protein. Recombinant human bone morphogenetic proteins (rhBMPs) are further preferred because they are available in large quantities and do not transmit infectious diseases. Most preferably, the bone morphogenetic protein is a rhBMP-2, rhBMP-4 or heterodimers thereof. However, any bone morphogenetic protein is contemplated, including bone morphogenetic proteins designated as BMP-1 through BMP-18.

BMPs are available from Genetics Institute, Inc., Cambridge, Massachusetts and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Pat. Nos. WO93/00432 to Wozney et al.; WO94/26893 to Celeste et al.; and WO94/26892 to Celeste et al. All bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In other forms of the invention, the pharmacological agent may be one that is used for treating various spinal conditions, including infected spinal cords, cancerous spinal cords and osteoporosis. Such agents include antibiotics, analgesics and anti-inflammatory drugs, including steroids. Other such agents are well know to the skilled artisan. These agents are also used in therapeutically effective amounts that will treat the various conditions and the symptoms they cause. Such amounts may be determined by the skilled artisan depending on the specific case.

The pharmacological agents are preferably dispersed within the hydrogel, or other hydrophilic, implant for in vivo release, and/or, with respect to implants with an elastomeric resorbable outer shell or those with a flexible supporting band, may be dispersed in either the band, the outer shell, or both. The hydrogel can be cross-linked chemically, physically, or by a combination thereof, in order to achieve the appropriate level of porosity to release the pharmacological agents at a desired rate. The agents may be released upon cyclic loading, and, in the case of implants including a resorbable outer shell, upon resorption of the shell. The pharmacological agents may be dispersed in the implants by adding the agents to the solution used to form the implant, as long as the processing conditions will not adversely affect the agent. Alternatively, the implants may be soaked in an appropriate solution containing the agent, or by other appropriate methods known to the skilled artisan.

Figure 26:
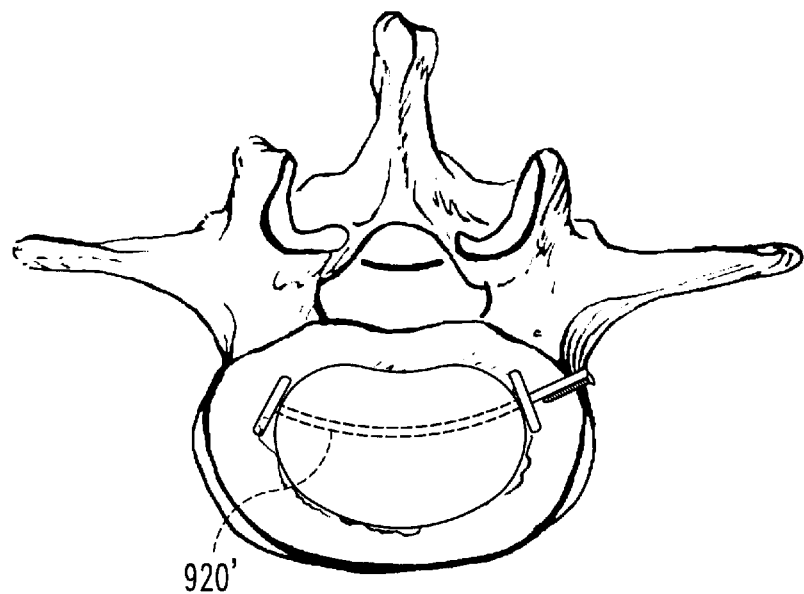
FIG. 26 depicts a top, cut-away view of an alternative embodiment of a device for anchoring a spinal implant that is implanted in an intervertebral disc space.
Figure 27:
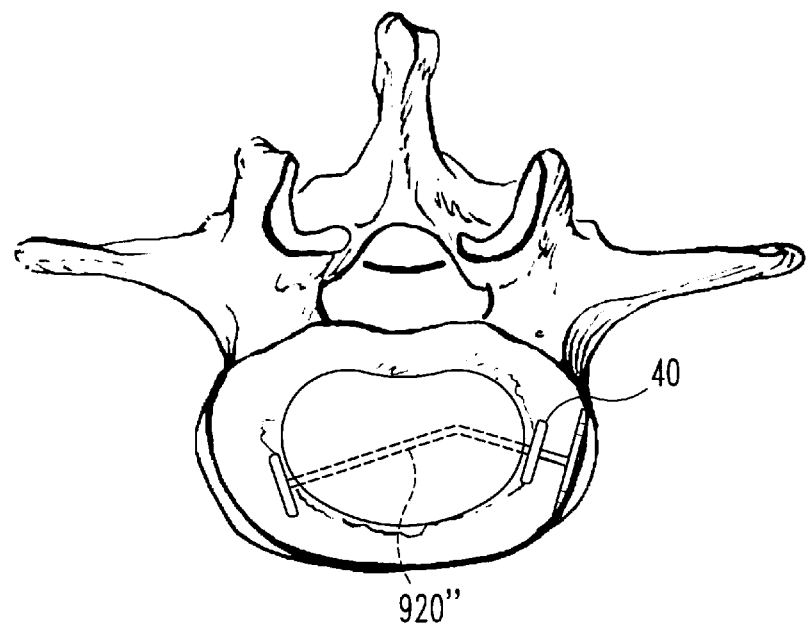
FIG. 27 shows a top, cut-away view of an alternative embodiment of a device for anchoring a spinal implant that is implanted in an intervertebral disc space.
Figure 28:
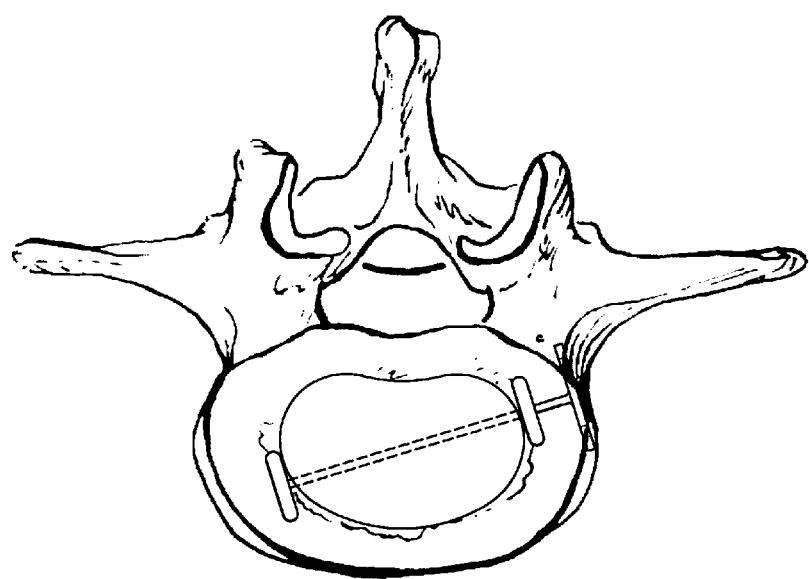
FIGS. 28–31 depicts cut-away, top views of anchoring devices, along with anchored implants, inserted via posterior, lateral, oblique and anterior approaches, respectively.
Figure 29:
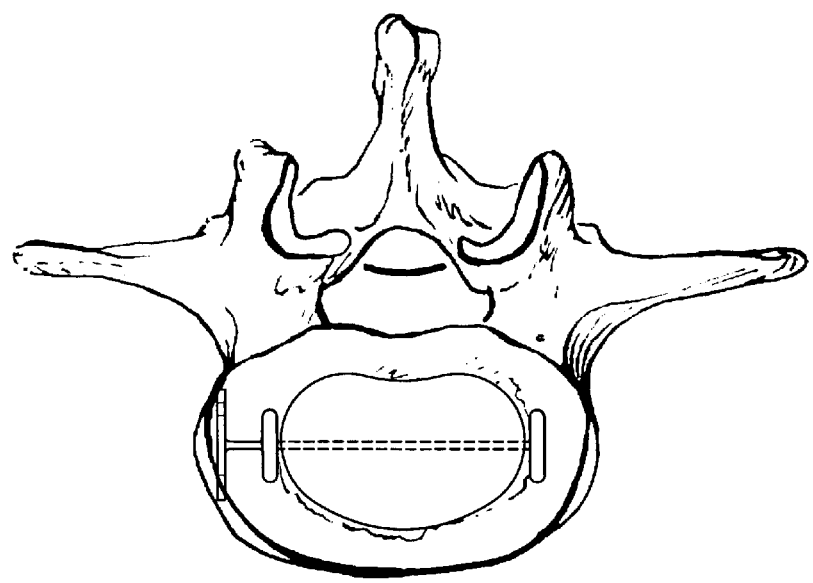
Figure 30:
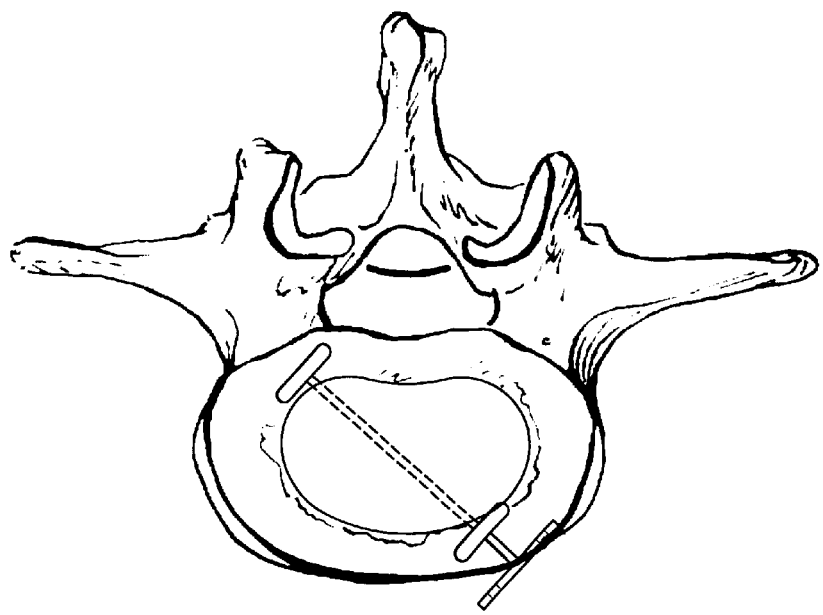
Figure 31:
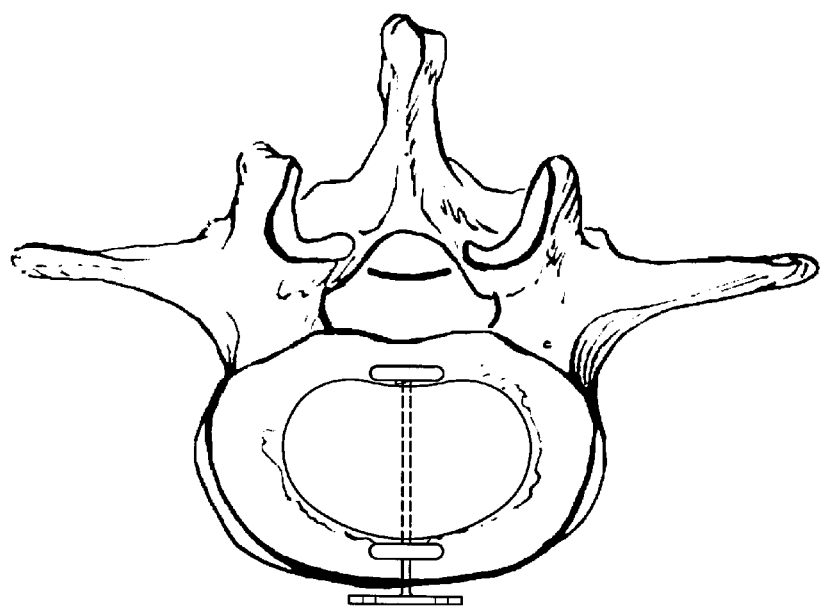
Figure 32:
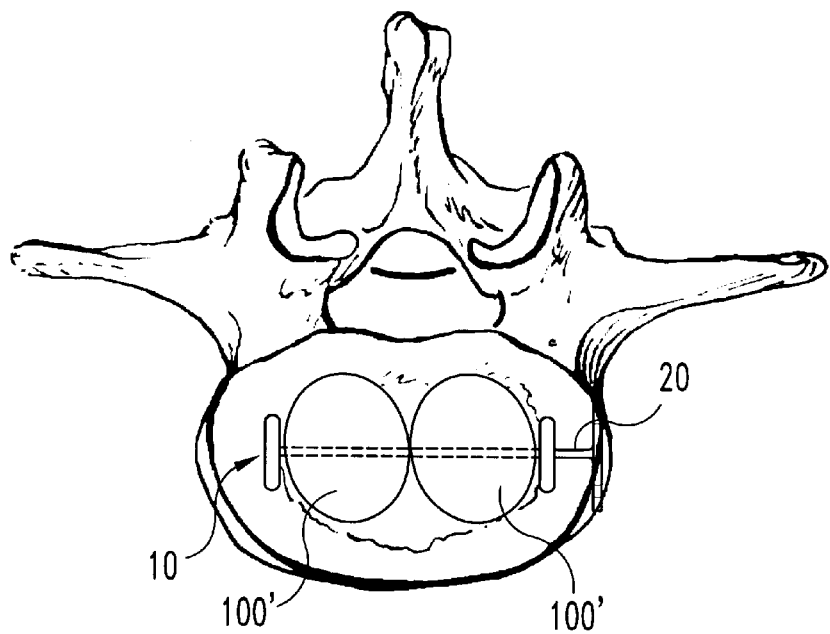
FIG. 32 depicts a top, cut-away view of a device for anchoring a spinal implant that is implanted in an intervertebral disc space, wherein two implants are advantageously anchored.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, in addition to being straight, the elongated bodies of the anchoring device may exhibit other advantageous shapes as shown in FIGS. 26 and 27. As seen in FIG. 26, anchoring rod 920' is arcuate. As seen in FIG. 27, anchoring rod 920" has a bend adjacent to securing member 40. Other bent or angled anchoring components may be understood by those of ordinary skill in the art, and such embodiments are encompassed by this invention. Furthermore, the devices described herein may be inserted and anchored via a wide variety of approaches, including posterior, lateral, oblique and anterior as shown in FIGS. 28–31, respectively. Moreover, the nucleus pulposus implant systems may include one or more implants disposed on the anchoring rods of the anchoring devices described herein. As seen in FIG. 32, two implants 100' are disposed on anchoring rod 20 of anchoring device 10. Thus, typically at least one implant is included in the implant systems described herein.

Figure 33:
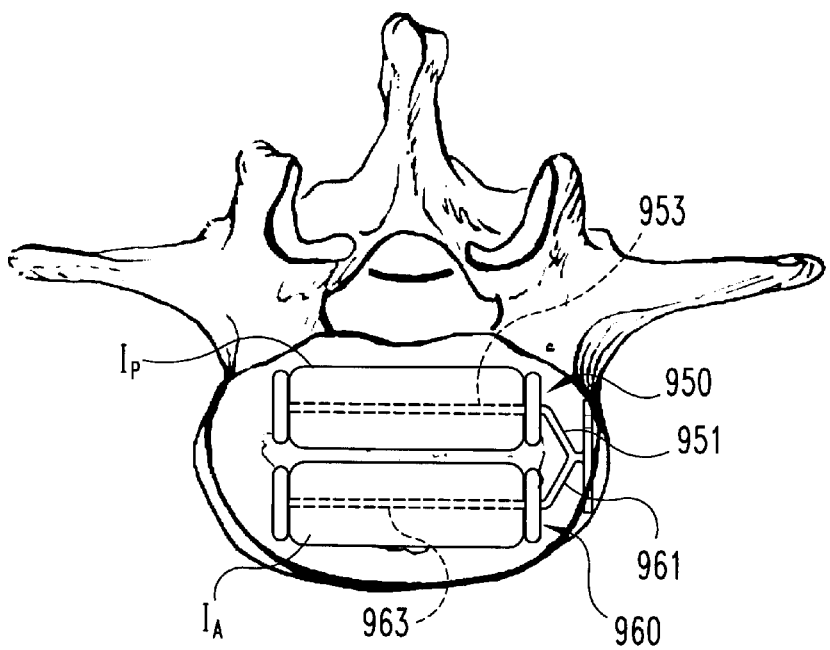
FIG. 33 depicts a top, cut-away view of an alternative embodiment of a device for anchoring a spinal implant, wherein two devices are used to anchor two spinal implants.

Additionally, in other forms of the invention, the spinal implant systems may include one or more elastic bodies and one or more anchoring devices. Referring now to FIG. 33, two anchoring devices are included in the system along with two elastic bodies, each elastic body disposed on a different anchoring device 950 or 960. Each anchoring device may be independently anchored to an adjacent vertebra. In alternative embodiments, first ends 951 and 961 of anchoring rods 953 and 963, respectively, may be connected, or otherwise attached to each other to form a single extension, or end, of the anchoring rods, which may in turn be attached to an adjacent vertebra or bracket as described herein. The latter case is shown in FIG. 33, wherein first ends 951 and 961 of elongated bodies 953 and 963, respectively, of anchoring devices 950 and 960 are integral with each other. Utilizing such a system with anterior and posterior implants $I_A$ and $I_P$, respectively, implants having different heights may be used to create or maintain lordosis. For example, if a cylindrical implant is desired, anterior implant $I_A$ may have a larger diameter, and thus a larger height, than posterior implant $I_P$.

All references cited herein are indicative of the level of skill in the art and are hereby incorporated by reference in their entirety.

What is claimed is:

1. An implant system for implantation into an intervertebral disc space, comprising:

(a) an elastic spinal implant having a longitudinal axis; and (b) an anchoring component, said component comprising an anchoring rod and at least one securing member attached to said anchoring rod, said anchoring rod having a first end, a second end, a longitudinal axis and extending at least partially through said implant, said anchoring component securable to an adjacent vertebra, wherein said anchoring rod is comprised of a metallic material selected from a shape memory material, titanium alloy, titanium, stainless steel, cobalt chrome alloy and combinations thereof.

2. The system of claim 1, wherein said shape memory material is a shape memory alloy that exhibits superelastic behavior.

3. An implant system for implantation into an intervertebral disc space, comprising:
  (a) an elastic spinal implant having a longitudinal axis;
  (b) an anchoring component, said component comprising an anchoring rod and at least one securing member attached to said anchoring rod, said anchoring rod having a first end, a second end, a longitudinal axis and extending at least partially through said implant, said anchoring component securable to an adjacent vertebra, and
  (c) a peripheral supporting band disposed circumferentially about said implant.

4. An implant system for implantation into an intervertebral disc space, comprising:
  (a) an elastic spinal implant having a longitudinal axis; and
  (b) an anchoring component, said component comprising an anchoring rod and at least one securing member attached to said anchoring rod, said anchoring rod having a first end, a second end, a longitudinal axis and extending at least partially through said implant, said anchoring component securable to an adjacent vertebra, wherein said first end of said anchoring rod is securable to an adjacent vertebra.

5. An implant system for implantation into an intervertebral disc space, comprising:
  (a) an elastic spinal implant having a longitudinal axis; and
  (b) an anchoring component, said component comprising an anchoring rod and at least one securing member attached to said anchoring rod, said anchoring rod having a first end, a second end, a longitudinal axis and extending at least partially through said implant, said anchoring component securable to an adjacent vertebra, wherein said anchoring component further includes a bracket, said first end of said anchoring rod securable to said bracket.

6. An implant system for implantation into an intervertebral disc space, comprising:
  (a) an elastic spinal implant having a longitudinal axis;
  (b) an anchoring component, said component comprising an anchoring rod and at least one securing member attached to said anchoring rod, said anchoring rod having a first end, a second end, a longitudinal axis and extending at least partially through said implant, said anchoring component securable to an adjacent vertebra; and
  (c) a tension band, said tension band secured to said anchoring component and to an adjacent vertebra.

7. A method of anchoring a spinal implant, comprising:
  (a) providing an elastic spinal implant and an anchoring component, wherein said elastic spinal implant comprises an elastic body and a peripheral supporting band, said peripheral supporting band disposed circumferentially about said elastic body for reducing deformation of said body, and wherein said anchoring component comprises an anchoring rod and at least one securing member attached to said anchoring rod, said anchoring rod having a first end, a second end, and a longitudinal axis, said anchoring component securable to an adjacent vertebra;
  (b) extending said anchoring rod at least partially through said implant; and
  (c) securing said anchoring component to an adjacent vertebra.

8. A method of anchoring a spinal implant, comprising:
  (a) providing an elastic spinal implant and an anchoring component, said component comprising an anchoring rod and at least one securing member attached to said anchoring rod, said anchoring rod having a first end, a second end, and a longitudinal axis, said anchoring component securable to an adjacent vertebra, wherein said anchoring rod is comprised of a metallic material, a non-metallic material, or a combination thereof;
  (b) extending said anchoring rod at least partially through said implant; and
  (c) securing said anchoring component to an adjacent vertebra.

9. The method of claim 8, wherein said metallic material is selected from a shape memory material, titanium alloy, titanium, stainless steel, cobalt chrome alloy and combinations thereof.

10. A method of anchoring a spinal implant, comprising;
  (a) providing an elastic spinal implant and an anchoring component, said component comprising an anchoring rod and at least one securing member attached to said anchoring rod, said anchoring rod having a first end, a second end, and a longitudinal axis, said anchoring component securable to an adjacent vertebra; wherein said first end of said anchoring rod is securable to an adjacent vertebra;
  (b) extending said anchoring rod at least partially through said implant; and
  (c) securing said anchoring component to an adjacent vertebra.

11. A method of anchoring a spinal implant, comprising;
  (a) providing an elastic spinal implant and an anchoring component, said component comprising an anchoring rod and at least one securing member attached to said anchoring rod, said anchoring rod having a first end, a second end, and a longitudinal axis, said anchoring component securable to an adjacent vertebra; wherein said device further includes a bracket, said first end of said anchoring rod securable to said bracket;
  (b) extending said anchoring rod at least partially through said implant; and
  (c) securing said anchoring component to an adjacent vertebra.

* * * * *